United States Patent
Gong et al.

(10) Patent No.: US 6,479,490 B2
(45) Date of Patent: Nov. 12, 2002

(54) 3-INDOLYL-4-PHENYL-1H-PYRROLE-2,5-DIONE DERIVATIVES AS INHIBITORS OF GLYCOGEN SYNTHASE KINASE-3β

(75) Inventors: Leyi Gong, San Mateo, CA (US); Andrew Grupe, Redwood City, CA (US); Gary Allen Peltz, Redwood City, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/916,706

(22) Filed: Jul. 27, 2001

(65) Prior Publication Data

US 2002/0052397 A1 May 2, 2002

Related U.S. Application Data

(60) Provisional application No. 60/221,058, filed on Jul. 27, 2000.

(51) Int. Cl.⁷ ................... A61K 31/535; A61K 31/40; C07D 413/00; C07D 401/60; C07D 209/02
(52) U.S. Cl. ................... 514/235.5; 514/323; 514/414; 544/143; 546/187; 548/466
(58) Field of Search .............. 514/235.5, 323, 514/414; 544/143; 546/187; 548/466

(56) References Cited

U.S. PATENT DOCUMENTS

| | | |
|---|---|---|
| 5,057,614 A | 10/1991 | Davis et al. |
| 5,399,712 A | 3/1995 | Hill |
| 5,721,230 A | 2/1998 | Harris et al. |
| 5,721,245 A | 2/1998 | Harris et al. |

FOREIGN PATENT DOCUMENTS

| | | |
|---|---|---|
| EP | 0 540956 A1 | 5/1993 |
| EP | 0 384349 B1 | 4/1994 |
| EP | 0 616032 A2 | 9/1994 |
| EP | 0 624586 A1 | 11/1994 |
| WO | WO 97/22360 | 6/1997 |
| WO | WO 97/41854 | 11/1997 |
| WO | WO 98/11103 | 3/1998 |
| WO | WO 00/38675 | 7/2000 |

OTHER PUBLICATIONS

Hoeflich, et al., "Requirement for glycogen synthase kinase–3β in cell survival and NF–kB activation," *Nature*, vol. 406 (Jul. 6, 2000), pp 86–90.

Faul, et al., "aA New One Step Synthesis of Maleimides by Condensation of Glyoxylate Esters with Acetamides," *Tetrahedron Letters*, vol. 40 (1999), pp 1109–1112.

Davis, et al., "Inhibitors of Protein Kinase C. 1.¹ 2,3 Bisarylmaleimides," *J. Med. Chem.*, vol. 35:1 (1992) pp 177–184.

Harris, et al., "Oxidative Cyclisations with Palladium Acetate. A Short Synthesis of Staurosporine Aglycone," *Tetrahedron Letters*, vol. 34:51 (1993) pp 8361–8364.

Klein, et al., "A molecular mechanism for the effect of lithium on development," *Proc. Natl. Acad. Sci. USA*, vol. 93 (Aug. 1996) pp 8455–8459.

*Primary Examiner*—T. A. Solola
*Assistant Examiner*—Joseph Murray
(74) *Attorney, Agent, or Firm*—Rohan Peries

(57) ABSTRACT

This invention relates to inhibitors of glycogen synthase kinase-3β, methods of treating diseases characterized by an excess of Th2 cytokines, and to 3-indolyl-4-phenyl-1H-pyrrole-2,5-dione derivatives of Formula (I):

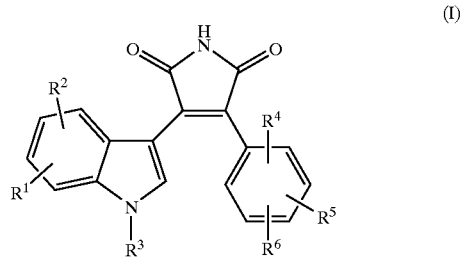

(I)

that are inhibitors of glycogen synthase kinase -3β, pharmaceutical compositions containing them, methods for their use and methods for preparing these compounds.

30 Claims, 3 Drawing Sheets

II-2:

II-1:

3-INDOLYL-4-PHENYL-1H-PYRROLE-2,5-DIONE DERIVATIVES AS INHIBITORS OF GLYCOGEN SYNTHASE KINASE-3β

CROSS-REFERENCE TO RELATED APPLICATION

Pursuant to 35 U.S.C. §119(e), this application claims priority to the filing date of the U.S. Provisional Patent Application Ser. No. 60/221,058 filed on Jul. 27, 2000, the disclosure of which is herein incorporated by reference.

BACKGROUND OF THE INVENTION

1. Field of the Invention

The present invention is directed to 3-indolyl-4-phenyl-1H-pyrrole-2,5-dione derivatives that inhibit glycogen synthase kinase-3β (GSK-3β) and are therefore useful in the treatment of mammals having disease states mediated by it. The present invention is also directed to pharmaceutical compositions containing these compounds, methods for preparing them, and methods for their use, in particular methods of treatment of diseases characterized by excess Th2 cytokines and/or an excess IgE production.

2. State of the Art

Glycogen synthase kinase (GSK) is a serine/threonine kinase for which two isoforms, α and β, have been identified. Glycogen synthase kinase -3β (GSK-3β) was originally identified as a protein kinase which phosphorylated and inactivated glycogen synthase a key enzyme regulating insulin-stimulated glycogen synthesis ((see Embi et al., *Eur. J. Biochem.* 107, 519–527, (1980); Rylatt et al., *Eur. J. Biochem.* 107, 529–537, (1980); and Vandenheede et al., *J. Biol. Chem.* 255, 11768–11774, (1980)). Subsequently, it was discovered that GSK-3β is inhibited upon insulin activation thereby allowing the activation of glycogen synthase. Therefore, inhibition of GSK-3β stimulates insulin-dependent processes and is useful in the treatment of type 2 diabetes which is characterized by decreased sensitivity to insulin and an increase in blood glucose level. A number of drugs such as 5-iodotubercidin®, metformin®, troglitazonem®, have been used to treat diabetes. These drugs however have limited application because metformin® can cause hypoglycemia, troglitazonem® can cause severe hepatoxicity and 5-iodotubercidin®, a GSK-3 inhibitor, inhibits other serine/threonine and tyrosine kinases.

Recently, it has been discovered that GSK-3β plays a role in pathogenesis of Alzheimer's disease ((see Lovestone et al., *Current Biology*, 4, 1077–86 (1994), Brownlees et al., *Neuroreport*, 8, 3251–3255 (1997), Takashima et al., *PNAS* 95, 9637–9641 (1998), and Pei et al., *J Neuropathol. Exp.*, 56, 70–78 (1997)) and bipolar disorder (see Chen et al., *J. Neurochemistry*, 72, 1327–1330 (1999)). It has also been discovered that GSK-3β is involved in blocking of early immune response gene activation via NF-AT and regulation of apoptosis (see Beals et al., *Science*, 275, 1930–33 (1997) and Pap, M. et al. *J. Biochem.* 273, 19929–19932, (1998)). Recently, it has also been discovered that GSK-3β is required for the NF-κB mediated survival response in the TNF-α signalling pathway involved in the proinflammatory response to infection ((Hoeflich et.al., *Nature*, 406, 86–90 (2000)).

Furthermore, GSK-3β is also known to regulate the degradation of a protein (β-catenin) which controls the activity of TCF family of transcription factors ((see., Dale,T. C., *Biochem. J.* 329, 209–223 (1998); Clevers, H. & van de Wetering, M., *Trends in Genetics* 13, 485–489 (1997); Staal, F. J. T. et al., *International Immunology* 11, 317–323 (1999)). The activity of this pathway has been shown to regulate the proliferation of colonic epithelial cells; and the biochemical data and clinical genetics demonstrate that it regulates the development of colon cancer.

Accordingly, there is a need for compounds that would inhibit GSK-3β and thereby provide a means for combating diseases mediated by it. This invention fulfills this and related needs.

SUMMARY OF THE INVENTION

The present invention is directed to 3-indolyl-4-phenyl-1H-pyrrole-2,5-dione derivatives that inhibit GSK-3β and are therefore useful in the treatment of mammals having disease states mediated by it such as diabetes, Alzheimer's disease, bipolar disorder, ischemia, traumatic brain injury, and immunodeficiency.

In addition, Applicants have discovered that inhibition of GSK-3β activity reduces the level of CD4+ T-helper 2 cells (Th2) which produce cytokines such as IL-4, IL-5, IL-13, and promote IgE production and eosinophil differentiation. This is an important discovery because it has been established that Th2 specific cytokines play a key role in the pathogenesis of diseases such as allergies and asthma. Therefore, the compounds of the present invention also provide a novel approach for the treatment of allergies and asthma.

Accordingly, in a first aspect, this invention is directed to 3-indolyl-4-phenyl-1H-pyrrole-2,5-dione derivatives represented by Formula (I):

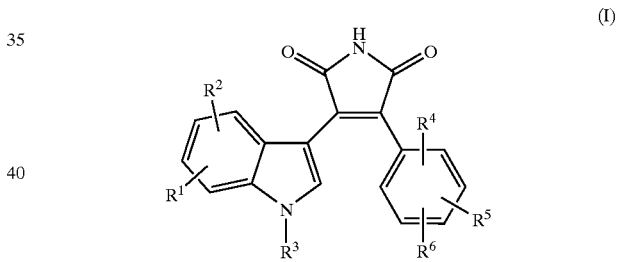

(I)

wherein:

$R^1$ and $R^2$ independently represent hydrogen, alkyl, halo, haloalkyl, alkylthio, hydroxy, alkoxy, cyano, nitro, amino, acylamino, monoalkylamino, or dialkylamino;

$R^3$ represents hydrogen, alkyl, cycloalkyl, heteroalkyl, —COR$^7$ (wherein R$^7$ is hydrogen or alkyl), or phenyl optionally substituted with one or two substituents independently selected from the group consisting of hydrogen, alkyl, haloalkyl, alkylthio, hydroxy, alkoxy, cyano, nitro, amino, acylamino, monoalkylamino, and dialkylamino;

$R^4$ and $R^5$ independently represent hydrogen, alkyl, halo, haloalkyl, alkylthio, hydroxy, alkoxy, cyano, nitro, amino, acylamino, monoalkylamino, or dialkylamino;

$R^6$ is heteroalkyl, heterocyclyl, heterocyclylalkyl, heteroalkylsubstituted heterocyclyl, heteroalkylsubstituted cycloalkyl, hetereosubstituted cycloalkyl, —OR$^8$, —S(O)$_n$R$^8$ (wherein n is 0 to 2; and R$^8$ is heteroalkyl, heteroaralkyl, heterocyclyl, or heterocyclylalkyl), —NR$^9$R$^{10}$ (wherein R$^9$ is hydrogen or alkyl and R$^{10}$ is heteroalkyl, heteroaralkyl, heterosubstituted cycloalkyl, heterocyclyl, or heterocyclylalkyl), or —X-

(alkylene)—Y—Z (wherein X is a covalent bond, —O—, —NH—, or —S(O)$_{n1}$— where n1 is 0 to 2, and Y is —O—, —NH—, or —S—, and Z is heteroalkyl or SiR$^{11}$R$^{12}$R$^{13}$ where R$^{11}$, R$^{12}$ and R$^{13}$ are independently hydrogen or alkyl), or R$^6$ together with R$^4$ forms a methylenedioxy or ethylenedioxy group when they are adjacent to each other; or a pharmaceutically acceptable salt thereof.

The compounds of the present invention exhibit surprisingly effective activity against GSK-3β. It is contemplated that the improved activity is due to their enhanced bioavailability and increased metabolic stability.

In a second aspect, this invention is directed to a method of treatment of a disease in a mammal treatable by administration of a GSK-3β inhibitor which method comprises administration of a therapeutically effective amount of a compound of Formula (I) or its pharmaceutically acceptable salt either alone or in combination with other pharmacologically active agents. In particular, the compounds of this invention are useful in treating respiratory diseases such as asthma.

In a third aspect, this invention is directed to pharmaceutical compositions containing a therapeutically effective amount of a compound of Formula (I) or its pharmaceutically acceptable salt and a pharmaceutically acceptable excipient.

In a fourth aspect, this invention is directed to the use of compounds of Formula (I) in the preparation of medicaments for use in the treatment of diseases mediated by GSK-3β.

In a fifth aspect, this invention provides processes for preparing compounds of Formula (I).

DETAILED DESCRIPTION OF THE INVENTION

Figure 1:
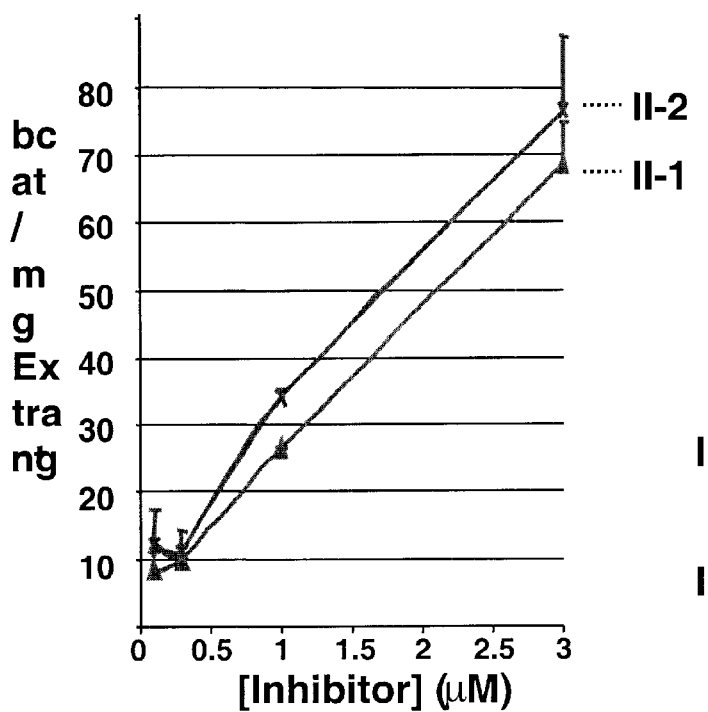
FIG. 1 shows the correlation between GSK inhibition by compounds of the invention and β-catenin levels in Jurkat T-cells.
Figure 1:
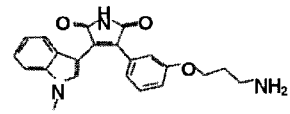
Figure 1:
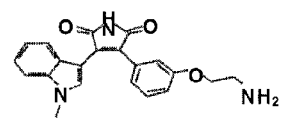

Definitions:

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a radical —OR where R is an alkyl as defined above e.g., methoxy, ethoxy, propoxy, butoxy and the like.

"Alkylthio" means a radical —SR where R is an alkyl as defined above e.g., methylthio, ethylthio, propylthio, butylthio, and the like.

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R$^1$ is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Cycloalkyl" refers to a saturated monovalent cyclic hydrocarbon radical of three to seven ring carbons e.g., cyclopropyl, cyclobutyl, cyclohexyl, 4-methylcyclohexyl, and the like.

"Cycloalkylalkyl" means a radical —R$^a$R$^b$ where R$^a$ is an alkylene group and R$^b$ is cycloalkyl group as defined herein, e.g., cyclohexylmethyl, and the like.

"Dialkylamino" means a radical —NRR$^1$ where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, or dialkylamino. Representative examples include, but are not limited to, 2-, 3-, or 4-hydroxycyclohexyl, 2-, 3-, or 4-aminocyclohexyl, 2-, 3-, or 4-sulfonamidocyclohexyl, and the like, preferably 4-hydroxycyclohexyl, 2-aminocyclohexyl, 4-sulfonamidocyclohexyl.

"Heteroalkylsubsituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. . Representative examples include, but are not limited to, 1-hydroxymethylcyclopentyl, 2-hydroxymethylcyclohexyl, and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro, cyano, More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —R$^a$R$^b$ where R$^a$ is an alkylene group and R$^b$ is a heteroaryl group as defined herein, e.g., pyridin-3-ylmethyl, imidazolylethyl, pyridinylethyl, 3-(benzofuran-2-yl)propyl, and the like.

"Heterocyclyl" means a saturated cyclic radical of 5 to 8 ring atoms in which one or two ring atoms are heteroatoms selected from NR (where R is independently hydrogen, alkyl, or heteroalkyl), O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, hydroxy, alkoxy, amino, monoalkylamino, dialkylamino, —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heteroalkylsubsituted heterocyclyl" means a heterocyclyl radical as defined herein wherein one, two or three hydrogen atoms in the heterocyclyl radical have been replaced with a heteroalkyl group with the understanding that the heteroalkyl radical is attached to the heterocyclyl radical via a carbon-carbon bond. Representative examples include, but are not limited to, 4-hydroxymethylpiperidin-1-yl, 4-hydroxymethylpiperazin-1-yl, 4-hydroxyethylpiperidin-1-yl, 4-hydroxyethylpiperazin-1-yl, and the like.

"Heterocyclylalkyl", "cycloalkylalkyl", or "phenylalkyl" means a radical —R$^a$R$^b$ where R$^a$ is an alkylene group and R$^b$ is phenyl or a heterocyclyl or cycloalkyl group as defined herein, e.g., tetrahydropyran-2-ylmethyl, 4-methylpiperazin-1-ylethyl, 3-piperidinylmethyl, 2,2-dimethyl-1,3-dioxoxolan-4-ylmethyl, benzyl, cyclohexylmethyl, and the like.

"Monoalkylamino" means a radical —NHR where R is an alkyl, cycloalkyl, or cycloalkylalkyl group as defined above, e.g., methylamino, (1-methylethyl)amino, cyclohexylamino, cyclohexylmethylamino, cyclohexylethylamino, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Phenylalkyl" means a radical —R$^a$R$^b$ where R$^a$ is an alkylene group and R$^b$ is a phenyl group as defined herein, e.g., benzyl and the like.

"Hydroxy or amino protecting group" refers to those organic groups intended to protect oxygen and nitrogen atoms against undesirable reactions during synthetic procedures. Suitable oxygen and nitrogen protecting groups are well known in the art e.g., trimethylsilyl, dimethyl-tert-butylsilyl, benzyl, benzyloxy-carbonyl (CBZ), tert-butoxycarbonyl (Boc), trifluoroacetyl, 2-trimethylsilylethanesulfonyl (SES), and the like. Others can be found in the book by T. W. Greene and G. M. Wuts, *Protecting Groups in Organic Synthesis,* Second Edition, Wiley, New York, 1991, and references cited therein..

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof.

For example, if the $R^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A compound of Formula (I) may act as a pro-drug. Prodrug means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The naming and numbering of the compounds of this invention is illustrated below.

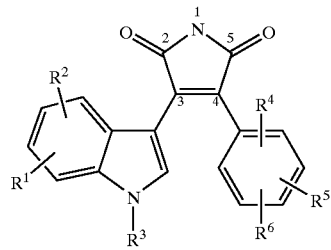

The nomenclature used in this application is generally based on the IUPAC recommendations. Since strict adherence to these recommendations would result in the names changing substantially when only a single substituent is changes, compounds have been named in a form that maintains consistency of nomenclature for the basic structure of the molecule. For example, a compound of Formula (I) where $R^1$, $R^2$, $R^4$ and $R^5$ are hydrogen, $R^3$ is methyl, $R^6$ is 2-hydroxyethylamino and is meta to the carbon attaching the phenyl ring to the pyrrole-2,5-dione ring is named 3-(1-methylindolyl)-4-[3-(2-hydroxyethylaminophenyl)-1H-pyrrole-2,5-dione.

a compound of Formula (I) where $R^1$, $R^2$, $R^4$ and $R^5$ are hydrogen, $R^3$ is methyl, $R^6$ is 2-hydroxyethylamino and is para to the carbon attaching the phenyl ring to the pyrrole-2,5-dione ring is named 3-(1-methylindolyl)-4-[4-(2-hydroxyethylaminophenyl)-1H-pyrrole-2,5-dione.

Representative compounds of this invention are as follows

I. Compounds of Formula (I) where $R^1$, $R^2$, $R^4$ and $R^5$=hydrogen, $R^3$=methyl, and $R^6$ is as defined below are:

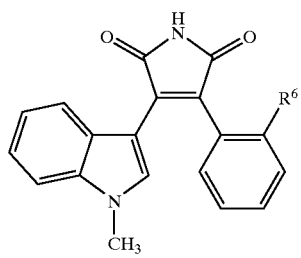

| Cpd. # | R⁶ | M. pt ° C. | Mass Spec. | Example |
|---|---|---|---|---|
| I-1 | 2,3-dihydroxypropoxy | 245–247.1 | 392 M⁺ | 1 |
| I-2 | 2,2-dimethyl-1,3-dioxolan-4-ylmethyloxy | 220.8–221.2 | 432 M⁺ | 2 |

II. Compounds of Formula (I) where $R^1$, $R^2$, $R^4$ and $R^5$=hydrogen, $R^3$=methyl, and $R^6$ is as defined below are:

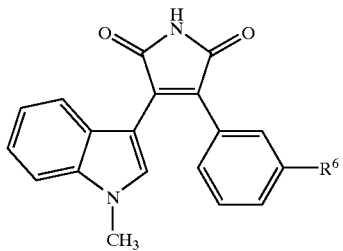

| Cpd. # | R⁶ | M. pt ° C. | Mass Spec. | Example |
|---|---|---|---|---|
| II-1 | 2-aminoethyloxy hydrochloride | 182.4–187 | 362 M⁺ | 6 |
| II-2 | 3-aminopropyloxy hydrochloride | | 375 M⁺ | 5 |
| II-3 | 2(R),3-dihydroxypropoxy | 177.7–178 | 392 M⁺ | 2 |
| II-4 | 2-morpholin-4-ylethyloxy | 197.7–199 | 431 M⁺ | 3 |
| II-5 | 2(S),3-dihydroxy-propoxy | 176.9–178.1 | 392 M⁺ | 2 |
| II-6 | (R)-2,2-dimethyl-1,3-dioxolan-4-ylmethyloxy | | 432 M+ | 1 |
| II-7 | (S)-2,2-dimethyl-1,3-dioxolan-4-ylmethyloxy | 186.8–187.4 | 432 M+ | 1 |
| II-8 | (RS)-2,2-dimethyl-1,3-dioxolan-4-yl-methylamino | | 431 M+ | 7 |
| II-9 | 2,3-dihydroxy-propylamino | 160–163.5 | 392 (M + H)⁺ | 7 |
| II-10 | 2,2-dimethyl-1,3-dioxan-5-ylamino | 201–203 | 431 M⁺ | 9 |
| II-11 | (RS)-2-hydroxy-1-hydroxymethylethylamino | 97.5–101 | 391 M+ | 10 |
| II-12 | (RS)-3-hydroxybutylamino | | 389 M+ | 14 |
| II-13 | (RS)-2-hydroxy-1-methylpropylamino | | 389 M+ | 15 |
| II-13A | tetrahydropyran-4-ylamino | | 401 M⁺ | 8 |
| II-14 | imidazol-2-ylmethylamino | | 397 M+ | 11 |
| II-15 | morpholin-4-yl hydrochloride | 205.3–212.6 | 388 M⁺ | 4 |
| II-16 | 3-(tert-butyl-dimethylsilyl-oxy)propylamino | 58–65 | 490 (M + H)⁺ | 12 |
| II-17 | 2-(tert-butyl-diphenylsilyl-oxy)ethylamino | | 600 (M + H)⁺ | 12 |
| II-18 | 3-hydroxypropylamino hydrochloride | 180–192 | 376 (M + H)⁺ | 13 |
| II-19 | 2-hydroxyethylamino hydrochloride | 170.3–170.6 | 362 (M + H)⁺ | 13 |
| II-20 | 3-hydroxypropyloxy | 150.2–152.6 | 377 (M + H)⁺ | 13 |
| II-21 | 3-(tert-butyl-dimethylsilyl-oxy)propyloxy | 151.2–151.7 | 491 (M + H)⁺ | 6 |
| II-22 | (RS)-1-hydroxymethylethyl-amino | 203.1–205.8 | 376 (M + H)⁺ | 15 |
| II-23 | 3-hydroxy-1-methylpropylamino | | 389 M⁺ | 14 |
| II-24 | (RS)-bis(2,3-dihydroxy-propyl)amino | | 466 (M + H)⁺ | 7 |
| II-25 | pyrrolidin-1-yl | | 372 M⁺ | 4 |
| II-26 | (S)-2-hydroxy-2-hydroxymethylethylamino | | 392 (M + H)⁺ | 7 |
| II-27 | 2(R),3-dihydroxy-propylamino.HCl | | 392 (M + H)⁺ | 7 |
| II-28 | 4-hydroxycyclohexylamino | | 415 M⁺ | 8 |
| II-29 | 4-hydroxypiperidin-1-yl | 136.0–141.0 | 402 (M + H)⁺ | 23 |
| II-30 | (R)-2,2-dimethyl-1,3-dioxolan-4-yl-methylsulfanyl | | 448 M⁺ | 18 |
| II-31 | (R)-2,3-dihydroxypropylsulfanyl | | 408 M⁺ | 21 |
| II-32 | (R)-2,2-dimethyl-1,3-dioxolan-4-yl-methylsulfinyl | | 465 (M + H)⁺ | 19 |
| II-33 | (R)-2,3-dihydroxypropylsulfinyl | | 425 (M + H)⁺ | 21 |
| II-34 | (R)-2,2-dimethyl-1,3-dioxolan-4-yl-methylsulfonyl | | 481 (M + H)⁺ | 20 |
| II-35 | (R)-2,3-dihydroxypropylsulfonyl | | 411 (M + H)⁺ | 21 |

III. Compounds of Formula (I) where $R^2$, $R^4$ and $R^5$=hydrogen, $R^1$, $R^3$ and $R^6$ are as defined below are:

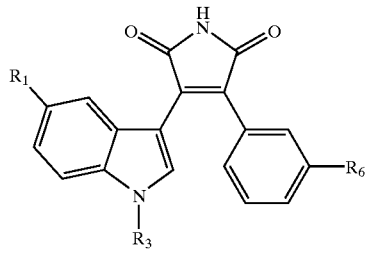

| Cpd. # | $R^1$ | $R^3$ | $R^6$ | M. pt ° C. | Mass Spec. | Example |
|---|---|---|---|---|---|---|
| III-1 | Chloro | methyl | (RS)-2,3-dihydroxypropylamino | 224.5–225.7 | 426 (M + H)+ | 16 |
| III-2 | fluoro | methyl | 3-aminopropyloxy hydrochloride | 223.2–225.0 | 410 (M + H)+ | 17 |
| III-3 | H | H | 2-(morpholin-4-yl)-ethoxy | | 417 (M + H)+ | 3 |
| III-4 | chloro | methyl | ((R)-2-hydroxy-2-hydroxymethyl)ethyloxy | | 427 (M + H)+ | 24 |
| III-5 | fluoro | methyl | ((R)-2-hydroxy-2-hydroxymethyl)ethyloxy | | 411 (M + H)+ | 24 |
| III-6 | fluoro | 3-hydroxy-propyl | (RS)-2,3-dihydroxy-propylamino | | 454 (M + H)+ | 22 |
| III-7 | methoxy | methyl | 2,3-dihydroxy-propylamino | | 421 | 25 |
| III-8 | methyl | methyl | 2,3-dihydroxy-propylamino | | 405 | 25 |
| III-9 | isopropoxy | methyl | 2,3-dihydroxy-propylamino | | 449 | 26 |

IV. Compounds of Formula (I) where $R^1$, $R^2$, $R^4$ and $R^5$=hydrogen, $R^3$=methyl, and $R^6$ is as defined below are:

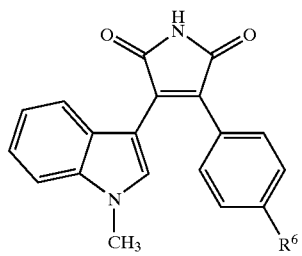

| Cpd. # | $R^6$ | m. pt ° C. | Mass Spec. | Example |
|---|---|---|---|---|
| IV-1 | (R)-2,2-dimethyl-1,3-dioxolan-4-yl-methyloxy | | 432 M+ | 1 |
| IV-2 | (RS)-2,3-dihydroxy-propylamino | 212–213.5 | | 7 |
| IV-3 | (RS)-2,2-dimethyl-1,3-dioxolan-4-yl-methylamino | 85–87.8 | | 7 |
| IV-4 | 3-hydroxybutylamino | 58–61.5 | 389 M+ | 13 |
| IV-5 | (RS)-1-methyl-2-hydroxy-ethylamino | | 375 | 15 |
| IV-6 | 2(R),3-dihydroxypropoxy | 220.3–222.7 | 392 M+ | 1 |

V. Additional compounds of Formula (I) where only one of $R^4$–$R^6$ is hydrogen are:
3-(1-methyl-indol-3-yl)-4-{3-((R)-2,3-dihydroxy-propoxyl)-2-methylphenyl}-1H-pyrrole-2,5-dione (Example 27); and
3-(1-methyl-indol-3-yl)-4-{3-((R)-2,3-dihydroxy-propoxyl)-2-nitrophenyl}-1H-pyrrole-2,5-dione (Example 28).

3-(1-methylindol-3-yl)-4-[5-((R)-2,3-dihydroxypropoxy)-2-nitrophenyl]-1H-pyrrole-2,5-dione (Example 28).

PREFERRED EMBODIMENTS

While the broadest definition of this invention is set forth in the Summary of the Invention, certain compounds of Formula (I) are preferred.

(A) A preferred group of compounds is that wherein $R^3$ is alkyl, preferably methyl or ethyl, more preferably methyl.

Within this group a more preferred group of compounds is that wherein $R^6$ group is at the 3- or 5-position of the phenyl ring, preferably $R^6$ is at the 3- position of the phenyl ring.

Within this group a more preferred group of compounds is that wherein $R^6$ is heteroalkyl.

Another more preferred group of compounds is that wherein $R^6$ is heterocyclylalkyl.

Yet another more preferred group of compounds is that wherein $R^6$ is —$OR^1$ (wherein $R^8$ is heteroalkyl or heterocyclylalkyl), preferably (RS), (R) or (S) 2-hydroxy-2-hydroxymethylethyloxy, 3-hydroxypropyloxy, 2-aminoethyloxy, 3-aminopropyloxy, 2-morpholin-4-ylethyloxy, or (R) or (S) 2,2-dimethyl-1,3-dioxolan-4-ylmethyloxy, more preferably (RS), (R) or (S) 2-hydroxy-2-hydroxymethylethyloxy.

Yet another more preferred group of compounds is that wherein $R^6$ is —$NHR^{10}$ (wherein $R^{10}$ is heteroalkyl, heterocyclyl, or heterocyclylalkyl), preferably (RS), (R) or (S) 2-hydroxy-2-hydroxymethylethylamino, 2-hydroxyethylamino, 3-hydroxypropylamino, (RS), (R) or (S) 2,2-dimethyl-1,3-dioxolan-4-ylmethylamino, 2,2-dimethyl-1,3-dioxan-5-ylamino, 2-hydroxy-1-hydroxymethylethylamino, 3-hydroxybutylamino, imidazol-2-ylmethylamino, or tetrahydropyran-4-ylamino, more preferably (RS), (R) or (S) 2-hydroxy-2- hydroxymethylethylamino, (RS), (R) or (S) 2,2-dimethyl-1, 3-dioxolan-4-ylmethylamino, 3-hydroxybutylamino, or 2-hydroxy-1-hydroxymethylethylamino.

Yet another more preferred group of compounds is that wherein $R^6$ heterocyclyl or —X— (alkylene)-Y-heteroalkyl (wherein X is a covalent bond, —O— or —NH— and Y is —O— or —NH—), preferably heterocyclyl, more preferably morpholin-4-yl or pyrrolidin-1-yl.

Within these preferred and more preferred groups of compounds, an even more preferred group of compounds is that wherein:

$R^1$ and $R^2$ are hydrogen; or $R^1$ is halo, preferably chloro and is located at the 5-position of the indole ring and $R^2$ is hydrogen; and $R^4$ and $R^5$ are at the 2- and the 6-positions of the phenyl ring respectively and are hydrogen, alkyl, halo, alkoxy, cyano or nitro, preferably hydrogen, chloro or fluoro, more preferably $R^4$ and $R^5$ are both hydrogen or one of $R^4$ and $R^5$ is fluoro and the other is hydrogen, or both of $R^4$ and $R^5$ are fluoro.

(B) Another preferred group of compounds is that wherein $R^6$ group is at the 3- or 5-position of the phenyl ring, preferably $R^6$ is at the 3-position of the phenyl ring.

Within this group a more preferred group of compounds is that wherein $R^6$ is heteroalkyl.

Another more preferred group of compounds is that wherein $R^6$ is heterocyclylalkyl.

Yet another more preferred group of compounds is that wherein $R^6$ is $OR^8$ (where in $R^8$ is heteroalkyl or heterocyclylalkyl), preferably (RS), (R) or (S) 2-hydroxy-2-hydroxymethylethyloxy, 3-hydroxypropyloxy, 2-aminoethyloxy, 3-aminopropyloxy, 2-morpholin-4-ylethyloxy, or (R) or (S) 2,2-dimethyl-1,3-dioxolan-4-ylmethyloxy, more preferably (RS), (R) or (S) 2-hydroxy-2-hydroxymethylethyloxy.

Yet another more preferred group of compounds is that wherein $R^6$ is —NHR$^{10}$ (wherein $R^{10}$ is heteroalkyl, heterocyclyl, or heterocyclylalkyl), preferably (RS), (R) or (S) 2-hydroxy-2-hydroxymethylethylamino, 2-hydroxyethylamino, 3-hydroxypropylamino, (RS), (R) or (S) 2,2-dimethyl-1,3-dioxolan-4-ylmethylamino, 2,2-dimethyl-1,3-dioxan-5-ylamino, 2-hydroxy-1-hydroxymethylethylamino, 3-hydroxybutylamino, imidazol-2-ylmethylamino, or tetrahydropyran-4-ylamino, more preferably (RS), (R) or (S) 2-hydroxy-2-hydroxymethylethylamino, (RS), (R) or (S) 2,2-dimethyl-1, 3-dioxolan-4-ylmethylamino, 3-hydroxybutylamino, or 2-hydroxy-1-hydroxymethylethylamino.

Yet another more preferred group of compounds is that wherein $R^6$ heterocyclyl or —X— (alkylene)-Y-heteroalkyl (wherein X is a covalent bond, —O— or —NH— and Y is —O— or —NH), preferably heterocyclyl, more preferably morpholin-4-yl or pyrrolidin-1-yl.

Within these preferred and more preferred groups of compounds, an even more preferred group of compounds is that wherein $R^3$ is alkyl, preferably ethyl or methyl, more preferably methyl.

Within these preferred, more preferred, and even more preferred groups of compounds, a particularly preferred group of compounds is that wherein:

$R^1$ and $R^2$ are hydrogen; or $R^1$ is halo, preferably chloro and is located at the 5-position of the indole ring and $R^2$ is hydrogen; and $R^4$ and $R^5$ are at the 2- and the 6-positions of the phenyl ring respectively and are hydrogen,alkyl, halo, alkoxy, cyano or nitro, preferably hydrogen, chloro or fluoro, more preferably $R^4$ and $R^5$ are both hydrogen, or one of $R^4$ and $R^5$ is fluoro and the other is hydrogen, or both of $R^4$ and $R^5$ are fluoro.

(C) Yet another preferred group of compounds is that wherein $R^1$ and $R^2$ groups are at the 5- and 7-positions of the indole ring respectively; $R^4$ an $R^5$ groups are at the 2- and the 6-positions of the phenyl ring respectively and the $R^6$ group is at the 3- or 5-position of the phenyl ring, preferably $R^6$ is at the 3-position of the phenyl ring.

Within this group a more preferred group of compounds is that wherein $R^6$ is heteroalkyl.

Another more preferred group of compounds is that wherein $R^6$ is heterocyclylalkyl.

Yet another more preferred group of compounds is that wherein $R^6$ is —OR$^8$ (wherein $R^8$ is heteroalkyl or heterocyclylalkyl), preferably (RS), (R) or (S) 2-hydroxy-2-hydroxymethylethyloxy, 3-hydroxypropyloxy, 2-aminoethyloxy, 3-aminopropyloxy, 2-morpholin-4-ylethyloxy, or (R) or (S) 2,2-dimethyl-1,3-dioxolan-4-ylmethyloxy, more preferably (RS), (R) or (S) 2-hydroxy-2-hydroxymethylethyloxy.

Yet another more preferred group of compounds is that wherein $R^6$is —NHR$^{10}$ (wherein $R^{10}$ is heteroalkyl, heterocyclyl, or heterocyclylalkyl), preferably (RS), (R) or (S) 2-hydroxy-2-hydroxymethylethylamino, 2-hydroxyethylamino, 3-hydroxypropylamino, (RS), (R) or (S) 2,2-dimethyl-1,3-dioxolan-4-ylmethylamino, 2,2-dimethyl-1,3-dioxan-5-ylamino, 2-hydroxy-1-hydroxymethylethylamino, 3-hydroxybutylamino, imidazol-2-ylmethylamino, or tetrahydropyran-4-ylamino, more preferably (RS), (R) or (S) 2-hydroxy-2-hydroxymethylethylamino, (RS), (R) or (S) 2,2-dimethyl-1, 3-dioxolan-4-ylmethylamino, 3-hydroxybutylamino, or 2-hydroxy-1-hydroxymethylethylamino.

Yet another more preferred group of compounds is that wherein $R^6$ heterocyclyl or —X— (alkylene)-Y-heteroalkyl (wherein X is a covalent bond, —O— or —NH— and Y is —O— or —NH), preferably heterocyclyl, more preferably morpholin-4-yl or pyrrolidin-1-yl.

Within these preferred and more preferred groups of compounds, an even more preferred group of compounds is that wherein $R^3$ is alkyl, preferably ethyl or methyl, more preferably methyl Within these preferred, more preferred, and even more preferred groups of compounds, a particularly preferred group of compounds is that wherein:

$R^1$ and $R^2$ are hydrogen; or $R^1$ is halo, preferably chloro and $R^2$ is hydrogen; and $R^4$ and $R^5$ are hydrogen, alkyl, halo, alkoxy, cyano or nitro, preferably hydrogen, chloro or fluoro, more preferably $R^4$ and $R^5$ are both hydrogen or one of $R^4$ and $R^5$ is fluoro and the other is hydrogen, or both of $R^4$ and $R^5$ are fluoro.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., U.S.A.), Bachem (Torrance, Calif., U.S.A.), Emka-Chemie, or Sigma (St. Louis, Mo., U.S.A.) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. (make sure lastest volumes included, any better book and suppliers of sm).

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of compounds of Formula (I)

Schemes 1–4 describe alternative methods to prepare the compounds of Formula (I).

Compounds of Formula (I) where $R^3$ is methyl, $R^6$ is —$NHR^{10}$, and other groups are as defined in the Summary of the Invention can be prepared as shown in Scheme 1 below.

Scheme 1

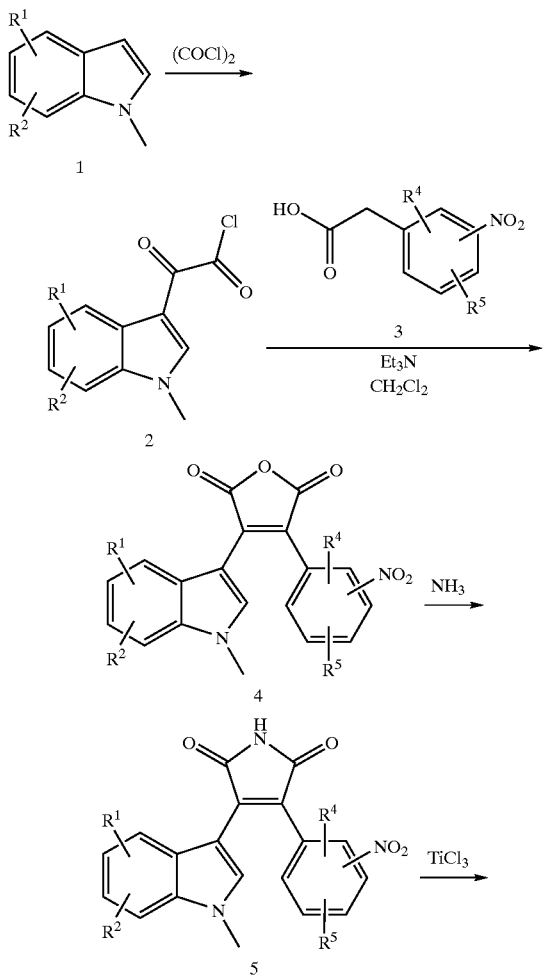

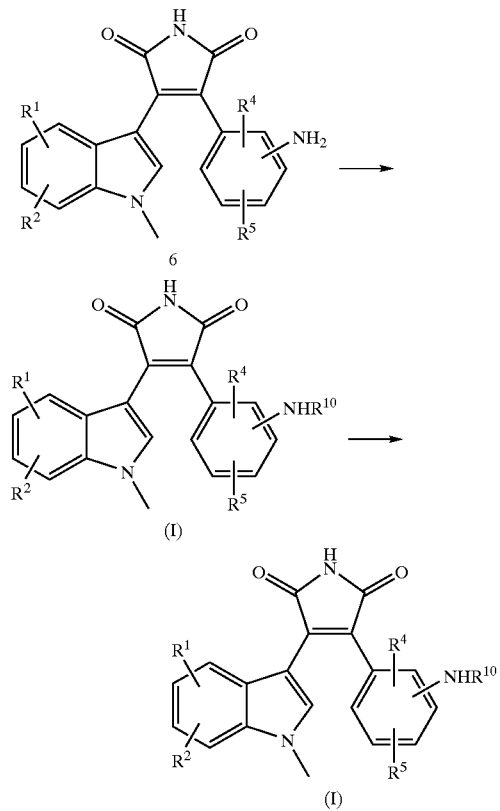

Acylation of N-methylindole of formula 1 with oxalyl chloride in an ethereal solvent such as diethyl ether provides a indole-3-glyoxylyl chloride of formula 2. The reaction is typically carried out between 0° C. and room temperature, preferably at 0° C. Compounds of formula 1 are commercially available or they can be prepared by methods well known in the art. For example, 1-methylindole, 4-methoxy-1-methylindole, and 5-bromo-1-methylindole are commercially available. 5-chloro-1-methylindole can be prepared by alkylation of commercially available 5-chloroindole by methods well known in the art such as treating 5-chloroindole with alkylhalide in the presence of a base such as sodium hydride in solvents such as dimethylformamide. Similarly, various other substituted indoles such as 5-fluoroindole and 4-, 5-, 6-, or 7-dimethylindole that are also commercially available and can be converted to the N-alkylindoles by alkylation as described above.

Condensation of 2 with a nitrophenylacetic acid of formula 3 provides 3-indolino-4-(nitrophenyl)-2,5-furandione of formula 4. The reaction is carried out in an inert organic solvent such as methylene chloride, chloroform, and the like and in the presence of a non-nucleophilic organic base such as triethylamine, diisopropylamine, and the like. Nitrophenylacetic acids of formula 3 are commercially available. For example 2-, 3-, and 4-nitrophenylacetic acids are commercially available from Aldrich. Other nitrophenyl acetic acids may be prepared from the corresponding cyano-halobenzenes by homologation of the cyano group to an acetic acid side chain by methods well known in the art. For example, 2,6-difluoro-3-nitrocyanobenzene can be converted to 2,6-difluoro-3-nitrophenylacetic acid as follows. Hydrolysis of the cyano group in 2,6-difluoro-3-nitrocyanobenzene under acidic hydrolysis reaction conditions provides 2,6-difluoro-3-nitrobenzoic acid which is then treated with a chlorinating agent such as oxalyl chloride to provide 2,6-difluoro-3-nitrobenzoyl chloride. Treatment of 2,6-difluoro-3-nitrobenzoyl chloride with diazomethane provides the corresponding diazoketone derivative which upon treatment with silver salt of benzoic acid (see Fieser Vol. 1, pg. 1004) in the presence of triethylamine in methanol provides methyl 2,6-difluoro-3-nitrophenylacetate. Hydrolysis of methyl 2,6-difluoro-3-nitrophenylacetate under basic hydrolysis reaction conditions (e.g., lithium hydroxide in aqueous methanol) provides the desired 2,6-difluoro-3-nitrophenylacetic acid.

Treatment of 4 with aqueous ammonium hydroxide in a high boiling organic solvent such as N,N-dimethylformamide provides 3-indolino-4-(nitrophenyl)-1H-pyrrole-2,5-dione of formula 5. The reaction is typically carried out between 130–140° C.

Reduction of the nitro group in 5 with a suitable reducing agent such as titanium trichloride in acetone provides a compound of formula 6 which is then converted to a compound of Formula (I) wherein $R^6$ is a group of formula —$NHR^{10}$ wherein $R^{10}$ is as defined in the Summary of the Invention by methods well known in the art. For example, a compound if Formula (I) where $R^{10}$ is a heteroaralkyl, heterocyclic, or heterocyclylalkyl group such as 2-imidazolylmethyl, 2,2-dimethyl-1,3-dioxan-5-yl, or 2,2-dimethyldioxolan-4-ylmethyl can be prepared by reacting a compound of formula 6 with 2-imidazole-carboxyaldehyde, 2,2-dimethyl-1,3-dioxan-5-one, and 2,2-dimethyldioxolan-4-carboxyaldehyde respectively, under reductive amination reaction conditions i.e., carrying out the reaction in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like). 2,2-Aldehydes and ketones such as 2-imidazolecarboxyaldehyde, 2,2-dimethyl-1,3-dioxan-5-one, and 2,2-dimethyldioxolan-4-carboxyaldehyde are commercially available. 2,2-Dimethyldioxolane-4-carboxyaldehyde can be prepared by the procedure described in Dumont, von R., et al., Helv. Chim. Acta, 66, 814, (1983).

As will be apparent to a person skilled in the art, a compound of Formula (I) can be converted to other compounds of Formula (I). For example, acidic hydrolysis of compound (I) wherein $R^{10}$ is 2,2-dimethyldioxolan-4-ylmethyl provides a compound of Formula (I) wherein $R^{10}$ is a 2,3-dihydroxy-propyl group.

Compounds of Formula (I) where $R^3$ is methyl, $R^6$ is heteroalkyl, heterocyclyl or —$OR^8$ wherein $R^8$ is heteroalkyl, heteroaralkyl, heterocyclyl, or heterocyclylalkyl, and other groups are as defined in the Summary of the Invention can be prepared as shown in Scheme 2 below.

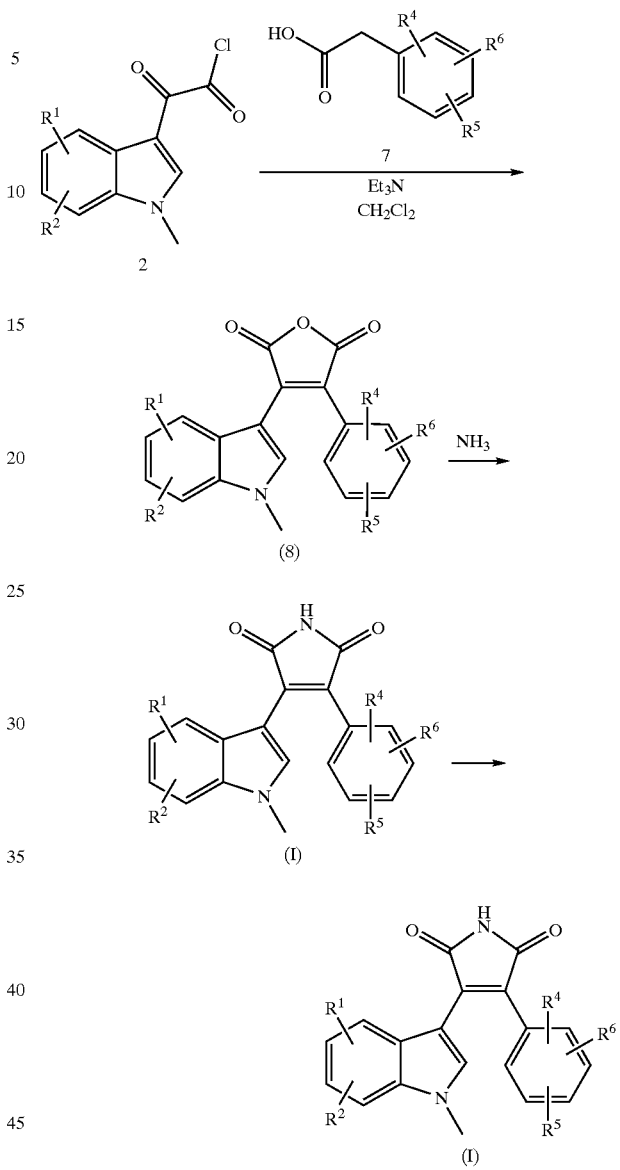

Reaction of a compound of formula 2 with a compound of formula 7 (where $R^6$ is heteroalkyl, heterocyclyl, or —$OR^8$ wherein $R^8$ is heteroalkyl, heteroaralkyl, heterocyclyl, or heterocyclylalkyl) under the reaction conditions described in Scheme 1 above provides a 3-indolino-4-phenyl-2,5-furandione of formula 8.

Compounds of formula 7 where $R^6$ is heteroalkyl, heterocyclyl, or —$OR^8$ (wherein $R^8$ is heteroalkyl, heteroaralkyl, heterocyclyl, or heterocyclylalkyl) can be prepared by methods well known in the art. For example, 3-heterocyclylphenylacetic acid can be prepared under catalytic amination reaction conditions by reacting methyl 3-bromophenylacetate with a suitable heterocycle (such as morpholine, piperidine, pyrrolidine, and the like) in the presence of a substituted phosphorous ligand such as 2,2-bis(diphenylphosphino)-1,1'-binaphthyl (BINAP) and a palladium catalyst such as tris(dibenzylideneacetone) dipalladium ($Pd_2(dba)_3$), followed by de-esterification of the resulting methyl 3-heterocyclylphenylacetate under basic hydrolysis reaction conditions.

3-(2-Aminoethyl)phenylacetic acid can be prepared by coupling methyl 3-bromophenylacetate with nitroethylene under Heck reaction conditions to give methyl 3-(2-nitrovinyl)phenyl acetate, followed by reduction of the alkene bond and the nitro group by methods well known in the art, e.g. catalytic hydrogenation followed by hydride reduction. Hydrolysis of methyl 3-(2-aminoethyl)phenylacetate under basic conditions then provides 3-(2-aminoethyl)phenylacetic acid. It will be recognized by a person skilled in the art that the amino group in 3-(2-aminoethyl)phenylacetic acid would be protected with a suitable protecting group prior to reacting it with compound 2.

Compounds of formula 7 where $R^6$ is —$OR^8$ (wherein $R^8$ is heteroaralkyl or heterocyclylalkyl) can be prepared by reacting hydroxyphenylacetic acid with an alkylating agent of formula $R^8X$ wherein $R^8$ is as defined above and X is a leaving group under alkylation reaction conditions such as halo (Cl, Br, I), tosylate, mesylate, triflate, and the like. The reaction is typically carried out in the presence of a base such as cesium carbonate, potassium carbonate and the like, and in an aprotic polar organic solvent such as acetonitrile, N-methylpyrrolidine, and the like. Alkylating agents such as 2-chloromethylpyridine, 2,2-dimethyl-1,3-dioxolan-4-ylmethyl p-toluenesulfonate, 1-(3-chloropropyl)piperidine, and 4-(2-chloroethyl)morpholine, and the like are commercially available.

Compound 8 which is then converted to a compound of Formula (I) as described in Scheme I above. Again, as discussed above, a compound of Formula (I) can be converted to other compounds of Formula (I). For example, acidic hydrolysis of compound (I) wherein $R^8$ is 2,2-dimethyldioxolan-4-ylmethyl provides a compound of Formula (I) wherein $R^8$ is a 2,3-dihydroxy-propyl group (i.e., $R^8$ is heteroalkyl group).

Alternatively, compounds of Formula (I) where $R^3$ is methyl and other groups are as defined in the Summary of the Invention can be prepared as shown in Scheme 3 below.

Scheme 3

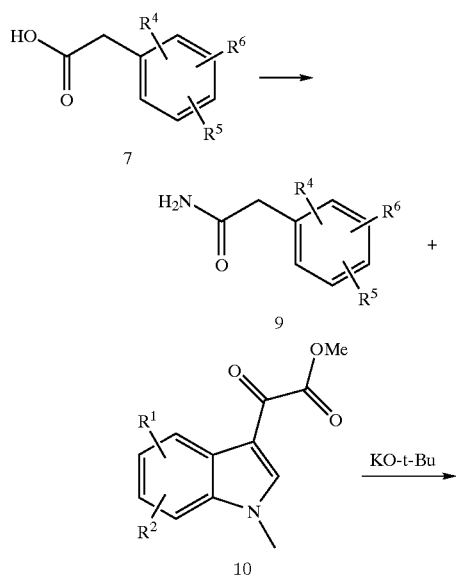

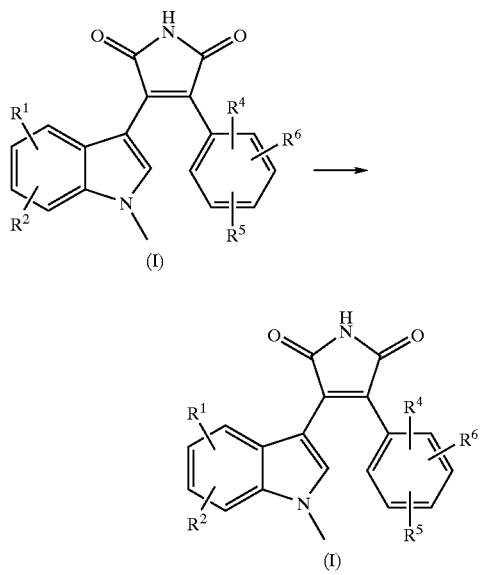

Reaction of a compound of formula 7 with a chlorinating agent such as oxalyl chloride in the presence of a catalytic amount of dimethylformamide and in an inert solvent such as dichloromethane, chloroform, and the like, provides the acid chloride. Treatment of the acid chloride with aqueous ammonia at 0° C. provides phenylacetamide of formula 9. Coupling of 9 with methyl indoleglyoxalate 10 provides a compound of Formula (I). The coupling reaction is carried out in the presence of a strong organic base such as tert-butoxide and in an ethereal organic solvent such as tetrahydrofuran and the like. Compounds of formula 10 where $R^1$ and $R^2$ vary can be prepared from 1-methylindole by the procedures described in Faul, M., et. al., *J. Org. Chem.*, 63, 6053–6058, (1998).

A compound of Formula (I) can be converted to other compounds of Formula (I) as described above. This synthetic route is particularly suitable for preparing compounds of Formula (I) wherein $R^6$ is heterocyclyl.

Alternatively, compounds of Formula (I) where $R^3$ is methyl and other groups are as defined in the Summary of the Invention can be prepared as shown in Scheme 4 below.

Scheme 4

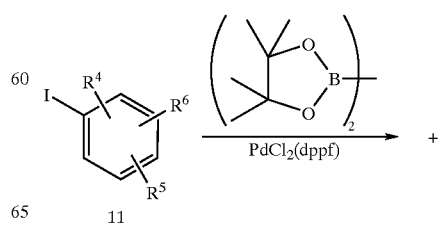

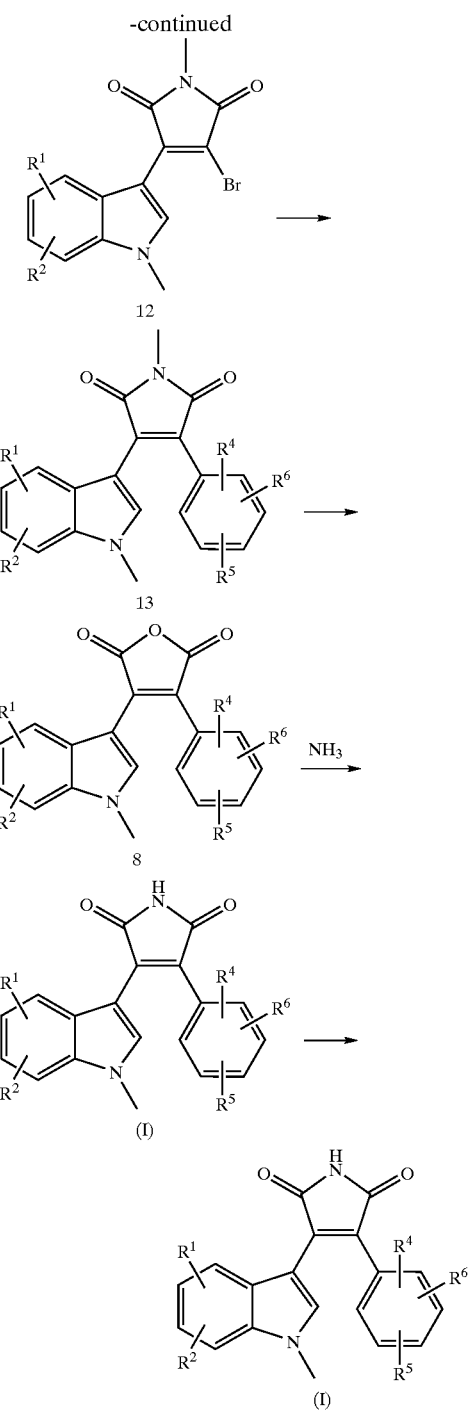

Treatment of an iodobenzene of formula 11 with bis(pinacolato)diborane in the presence of a palladium catalyst such as PdCl$_2$(dppf), followed by coupling of the resulting borate with a 4-bromo-3-(1-methylindol-3-ylmethyl)-1-methyl-pyrrole-2,5-dione 12 under Suzuki reaction conditions provides a 4-phenyl-3-(1-methylindol-3-ylmethyl)-1-methylpyrrole-2,5-dione 13. Compounds of formula 12 can be prepared by methods well known in the art. For example, 4-bromo-3-(1-methylindol-3-yl)-1-methylpyrrole-2,5-dione can be prepared by method described in Brenner, M. et al., *Tet. Lett.*, 44, 2887, (1988).

Treatment of 13 with a strong base such as sodium hydroxide, potassium hydroxide, and the like in an aqueous alcoholic solvent such as ethanol provides a 4-phenyl-3-(1-methylindol-3-ylmethyl)-1-H-pyrrole-2,5-dione 8 which is then converted to a compound of Formula (I) as described above.

Alternatively, compounds of Formula (I) where $R^3$ is methyl and other groups are as defined in the Summary of the Invention can be prepared as shown in Scheme 5 below.

Scheme 5

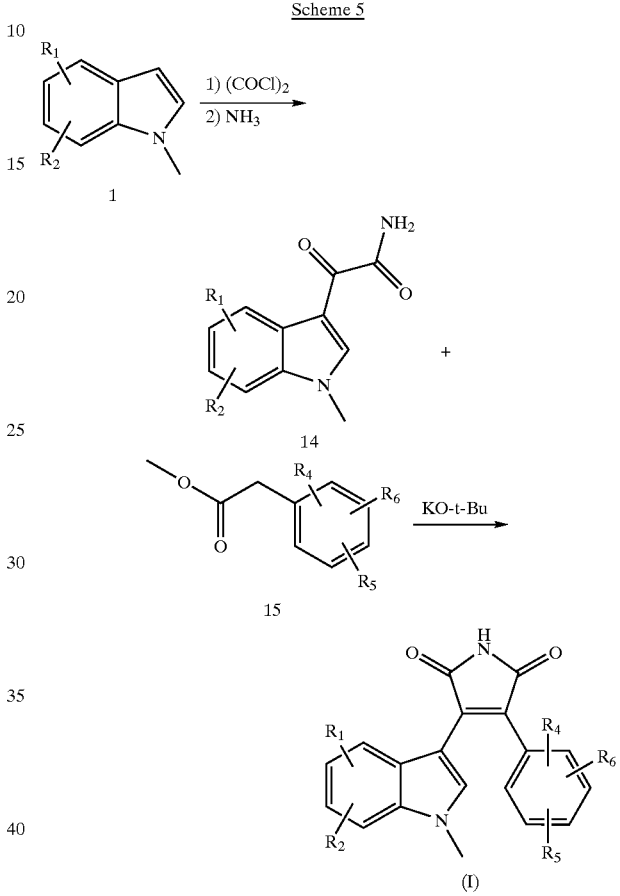

The acylation of N-methylindole of formula 1 with oxalyl chloride as described above, followed by quenching with aqueous ammonium at 0° C. provides a compound of formula 14 Coupling of 14 with a methyl phenylacetate of formula 15 provides a compound of Formula (I). The coupling reaction is carried out in the presence of a strong organic base such as tert-butoxide and in an ethereal organic solvent such as tetrahydrofuran and the like.

Utility, Testing, and Administration

Utility

The 3-indolyl-4-phenyl-1H-pyrrole-2,5-dione derivatives of Formula (I) inhibit GSK-3β. The compounds and compositions containing them are therefore useful in the treatment of diseases mediated by GSK-3β diseases such as Alzheimer's disease, obesity, diabetes, atherosclerotic cardiovascular disease, polycystic ovary syndrome, syndrome X, ischemia, traumatic brain injury, bipolar disorder, immunodeficiency and cancer.

In addition, Applicants have discovered that inhibition of GSK-3β activity reduces the level A. of CD4+ T-helper 2 cells (Th2) which produce cytokines such as IL-4, IL-5, IL-13, and promote IgE production and eosinophil differentiation. CD4 T-cells can differentiate into functionally distinct subsets with different profiles of cytokine production. Type 1 T Helper cells (Th 1) produce IFN-g and IL-2 and promote cell mediated immunity. Type 2 T Helper cells (Th2) produce IL-4 and IL-5 and promote IgE production and eosinophil differentiation. An imbalance in the type of T-cell response appears to underlie the susceptibility to asthma and allergic diseases. Through genetic studies Applicants have discovered that GSK-3β controls the activity of TCF7 (also known as TCF1 in the literature) thereby controlling whether or not naive T-cells differentiate into Th1 or Th2 cells. Furthermore, Applicants have discovered that inhibitors of GSK-3β inhibit Th2 cell development. This is an important discovery because it has been established that Th2 specific cytokines play a key role in the pathogenesis of diseases such as allergies and asthma. Specifically, IL-13 is implicated in airway hyper-responsiveness and mucus hypersecretion, as shown in murine studies of IL-13 delivery to the lungs of mice (Wills-Karp, M. et al., *Science* 282, 2258–2261 (1998); Grunig, G. et al., Science 282, 2261–2263 (1998)). Also, increased expression of IL-13 has been observed in airways of asthma patients which supports a role for IL-13 in the disease (Kroegel, C., et al., *European Respiratory Journal,* 9, 899–904, (1996). Furthermore, the total serum IgE levels and tissue eosinophilia, characteristic conditions of allergy and asthma, correlate with disease severity in atopic asthma patients (Yssel, H. et al., *Clinical and Experimental Allergy,* 28, Suppl 5: 104–109 (1998)). Prior to Applicants' discovery that GSK-3β controls TCF7 and thereby modulates Th2 cell differentiation, it was not known that inhibition of GSK-3β would provide a general method of treating dieseases such as asthma (particularly atopic asthma), allergies, allergic rhinitisis, all of which are caused by an excess of Th2 cells and there associated cytokines. As shown in the Examples below, Applicants have confirmed the ability of GSK-3β inhibitors to treat the asthmatic response in a variety of art-accepted in vivo models. Therefore, Applicants' invention encompasses the use of inhibitors of GSK-3β to treat wide range of allergies, asthma, and other diseases characterized by excess Th2 cytokines.

A murine genetic approach was used to identify a genetic locus that differentially regulated CD4 T cell subset differentiation and responsiveness to IL-12. The genetic background of the murine strain influences CD4 T cell development. The development of Th2 cells is favored in one strain (Balb/C) of mice, while T cells from another strain (B10 .D2) have a greater capacity to maintain IL-12 responsiveness and Th1 development in vivo and in vitro. Analysis of experimental intercrosses between Balb/C and B10.D2 mice expressing transgenic T cell antigen receptors led to identification of a locus located within a 0.5 cM region of murine chromosome 11 which controls maintenance of IL-12 responsiveness (Guler M. L. et al., *J. Immunol.* 162, 1339–1347, 1999). This region was syntenic to the locus on human chromosome 5q31, which has been associated with elevated serum IgE levels and susceptibility to asthma (Review: Cookson, W., Nature 402, Suppl. B5-B11, 1999). Positional cloning of this genetic locus was performed by analysis of the chromosomal sequence within this chromosomal region, and by analysis of gene expression.

We have demonstrated that TCF7 regulates T helper cell differentiation. TCF7, which is expressed only in T cells, was shown to be expressed in resting murine Th1, but not Th2 cells. This factor was also induced by IFN-gamma (FIG. 2B); and recognition elements for TCF7 were found in the promoter regions of genes expressed in Th1 cells; IFN-gamma, IFN-alpha, IL-18 and the beta-2 subunit of the IL12 receptor. We have also shown that inhibition of GSK-3β will increase the level of β-catenin in T cells. β-catenin does then accumulate in the nucleus and act as cofactor for TCF7 to activate gene transcription (Example 2, FIG. 1). Therefore, GSK-3, inhibitors will inhibit Th2 cell development. Wehave confirmed this by demonstrating that Th2 cytokine levels are reduced in cells treated with GSK-3β inhibitors (Examples 3 and 4).

Preferably, the GSK-3β inhibitors used for treatment of diseases characterized by excess Th2 cytokines will be selective for GSK-3β relative to other kinases, particularly PKC, p38 kinase, 1ck and cdk2, by a ratio of at least 10:1, more preferably 100:1 (based on their respective IC50's). Determination of the relative IC50's of a putative inhibitor may be accomplished by standard kinase activity assays well known to one of skill in the art. Such selective modulation permits the selective treatment of diseases characterized by excess Th2 cell production without affecting biological processes mediated by other kinases Furthermore, since GSK-3α and GSK-3β isoforms have 95% identical catalytic domains, it is contemplated that the compounds of the present invention would be useful in treating diseases mediated by GSK-3α.

Testing

The ability of the compounds of Formula (I) to inhibit GSK-3β was measured by in vitro assays such as ligand binding assay and inhibition of β-catenin degradation assay as described in detail in Biological Example 1 and 2 below. The ability of the compounds of this invention to inhibit secretion of IL-4 and IL-13 from human T-cells was measured by in vitro assay described in detail in Biological Example 3 below. The ability of the compounds of this invention to inhibit secretion of IL-4, IL-5 and IL-13 from murine T-cells was measured by in vitro assay described in detail in Biological Example 4 below. The ability of the compounds of this invention to inhibit leukocyte infiltration into the lungs was measured by in vivo assay described in detail in Biological Example 5 below. The ability of the compounds of this invention to reduce the IgE levels was measured by in vivo assay described in detail in Biological Example 6 below.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula (I) may range from approximately 1 mg to 5 mg per kilogram body weight of the recipient per day; preferably about 3 mg/kg/day. Thus, for administration to a 70 kg person, the dosage range would be about 70 to 350 mg/day, most preferably be about 200 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist which is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described below.

EXAMPLES

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "HCl" for hydrochloric acid, "DMF" for dimethylformamide, "NaOH" for sodium hydroxide, "KOH" for potassium hydroxide, "DMSO" for dimethylsulfoxide, "NaHCO$_3$" for sodium bicarbonate, "NaCl" for sodium chloride, "K$_2$CO$_3$" for potassium carbonate, "Na$_2$CO$_3$" for sodium carbonate, "LiOH" for lithium hydroxide, "Et$_3$N" for triethylamine, "NH$_3$ (aq)" for ammonium hydroxide, "CH$_2$Cl$_2$" for methylene chloride, "MeOH" for methanol, "EtOH" for ethanol, "Ph$_3$P" for triphenylphosphine, "CsCO$_3$" for cesium carbonate, "BINAP" for 2,2-bis-(diphenylphosphino)-1,1'-binaphthyl, "Pd$_2$(dba)$_3$" for tris(dibenzylideneacetone)-dipalladium, "NaCNBH$_3$" for sodium cyanoborohydride, "THF" for tetrahydrofuran, "Na$_2$SO$_4$" for sodium sulfate, "RT" for room temperature, "PTLC" for preparatory thin layer chromatography, "SiO$_2$" for silica gel, "EtOAc" for ethyl acetate, "APMA" for aminophenyl-mercuric acetate, "IL-1" for interleukin-1, and "RPMI" for Roswell Park Memorial Institute.

Synthetic Examples

Example 1

Synthesis of 3-(1-methylindol-3-yl)-4-[3-((R)-2,2-dimethyl-1,3-dioxolan-4-ylmethyloxy)phenyl]-1H-pyrrole-2,5-dione

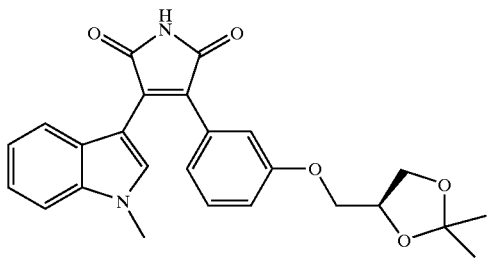

Step 1

Thionyl chloride (17 mL, 0.64 mol) was added dropwise to methanol at 0° C. After the completion of the addition, the reaction mixture was stirred at 0° C. for 10 min., and then 3-hydroxyphenylacetic acid (25 g, 0.16 mol) was added. The resulting reaction mixture was stirred at room temperature for 2 h. Volatiles were removed and the residue was partitioned between water and ethyl acetate. The organic layer was separated, washed with H₂O, NaHCO₃, and NaCl (sat.) and dried over Na₂SO₄. The crude product was purified on a silica gel column with 20% EtOAc in hexane to give methyl 3-hydroxyphenylacetate as a colorless oil (25 g, 94% yield).

Step 2

Methyl 3-hydroxyphenylacetate (20 g, 0.12 mol), (R)-2,2-dimethyl-1,3-dioxolan-4-ylmethyl p-tosylate (51.7 g, 1.5 eq.) and K₂CO₃ (50 g, 3eq.) in N-methylpyrrolidinone was heated at 96° C. overnight. The reaction mixture was cooled to room temperature, quenched with H₂O, and partitioned between H₂O and EtOAc. The organic layer was separated, washed with H₂O and NaCl (sat.), and then dried over Na₂SO₄. The crude product was purified on a silica gel column with 20% EtOAc in hexane to give methyl 3-((R)-2,2-dimethyl-1,3-dioxolan-4-ylmethyloxy)phenylacetate as an oil (23 g, 68% yield).

Step 3

To a solution of methyl 3-((R)-2,2-dimethyl-1,3-dioxolan-4-ylmethyloxy)phenyl-acetate (23 g, 0.08 mol) in methanol (80 mL) and water (5 mL) was added LiOH-H₂O (13.8 g, 4 eq.). After stirring the reaction mixture at room temperature for 4 h, the volatiles were removed under vacuo and the residue was partitioned between EtOAc and H₂0. The aqueous layer was separated, cooled with an ice bath, and then acidified with 10% aq. HCl. The acidic aqueous layer was extracted with EtOAc. The EtOAc layer was washed with NaCl (sat.), dried over Na₂SO₄, and concentrated to give 3-((R)-2,2-dimethyl-1,3-dioxolan-4-ylmethyloxy)phenylacetic acid as a white solid (22 g, >99% yield).

Step 4

Oxalyl chloride (1.05 eq., 4.15 mL) was added dropwise to a solution of N-methylindole (5.8 mL, 50 mmol) in diethyl ether (395 mL) at 0° C. Yellow precipitates were formed. After the completion of the addition, the reaction mixture was stirred at 0° C. for 30 min., and then the volatiles were removed under vacuo. The residue was re-dissolved in dichloromethane (375 mL) and added to a solution of 3-((R)-2,2-dimethyl-1,3-dioxolan-4-ylmethyloxy)phenylacetic acid (13.3 g, 50 mmol) and Et₃N (12.5 mL, 2.2eq.) in dichloromethane (375 mL) at 0° C. The resulting mixture was stirred at 0° C. and then allowed to warmed up slowly to room temperature. After stirring overnight, the volatiles were removed and the residue was purified on a silica gel column with dichloromethane to give 3-(1-methylindol-3-yl)-4-{3-((R)-2,2-dimethyl-1,3-dioxolan-4-ylmethyloxy)phenyl}furan-2,5-dione (5.4 g, 27% yield).

Step 5

3-(1-Methylindol-3-yl)-4-[3-((R)-2,2-dimethyl-1,3-dioxolan-4-ylmethyloxy)-phenyl]furan-2,5-dione (5.4 g, 13.7 mmol) was dissolved in DMF (50 mL) and was diluted with NH₃ (aq.) (100 mL). The reaction mixture was then heated at 140° C. for 5 h, cooled to room temperature and then diluted with water. The product was extracted with EtOAc and the organic layer was washed with NaCl (sat.) and dried over sodium sulfate to give the crude product which was further purified by re-crystallization from dichloromethane and hexane to give 3-(1-methylindol-3-yl)-4-[3-((R)-2,2-dimethyl-1,3-dioxolan-4-ylmethyloxy)phenyl]-1H-pyrrole-2,5-dione (5 g).

¹H NMR (DMSO-d6): δ 11.08 (s, NH), 8.04 (s, 1H), 7.49 (d, 1H, J=8.2), 7.22 (t, 1H, J=8.0), 7.12 (t, 1H, J=7.0), 6.97 (m, 3H), 6.76 (t, 1H, J=7.5), 6.33 (d, 1H, J=8.0), 4.23 (m, 1H), 3.96 (dd, 1H, J=6.5, 8.4), 3.91 (s, 3H), 3.77 (d, 1H, J=5.1), 3.60 (dd, 1H, J=6.1, 8.2), 1.30 (s, 3H), 1.27 (s, 3H); MS (EI): M⁺ 432.

Following the procedure described above, but substituting 3-hydroxyphenylacetic acid with 2-hydroxyphenylacetic acid gave 3-(1-methylindol-3-yl)-4-[2-((RS)-2,2-dimethyl-1,3-dioxolan-4-ylmethyloxy)phenyl]-1H-pyrrole-2,5-dione. ¹H NMR (DMSO-d6): δ 10.99 (s, NH), 8.03 (s, 1H), 7.46 (d, 1H, J=7.2), 7.38 (t, 1H, J=5.4), 7.27 (d, 1H, J=7.5), 7.11 (t, 1H, J=7.1), 7.03 (m, 2H), 6.64 (t, 1H, J=7.1), 6.32 (d, 1H, J=7.1), 4.3 (br.s. 2H), 3.88 (s, 3H), 3.68 (br.s. 2H), 3.2 (br.s. 1H), 1.19 (s, 6H); m.p. 220.8–221.2° C.; MS (EI): M⁺ 432;

Following the procedure described above, but substituting 3-hydroxyphenylacetic acid with 4-hydroxyphenylacetic acid gave 3-(1-methylindol-3-yl)-4-[4-((R)-2,2-dimethyl-1,3-dioxolan-4-ylmethyloxy)phenyl]-1H-pyrrole-2,5-dione. ¹H NMR (DMSO-d6): δ 11.00 (s, NH), 7.97 (s, 1H), 7.48 (d, 1H, J=6.3), 7.36 (d, 2H, J=8.9), 7.13 (t, 1H, J=7.2), 6.90 (d, 2H, J=8.9), 6.78 (t, 1H, J=7.2), 6.42 (d, 1H, J=8.0), 4.39 (m, 1H), 4.06 (m, 3H), 3.90 (s, 3H), 3.73 (m, 1H), 1.35 (s, 3H), 1.30 (s, 3H); MS (EI): M⁺ 432.

Following the procedure described above, but substituting (R)-2,2-dimethyl-1,3-dioxolan-4-ylmethyl p-tosylate with (S)-2,2-dimethyl-1,3-dioxolan-4-ylmethyl p-tosylate gave 3-(1-methylindol-3-yl)-4- [3-((S)-2,2-dimethyl-1,3-dioxolan-4-ylmethyloxy)phenyl]-1H-pyrrole-2,5-dione.

Example 2

Synthesis of 3-(1-methylindol-3-yl)-4-{3-[((R)-2-hydroxy-2-hydroxymethyl)ethyloxy]phenyl}-1H-

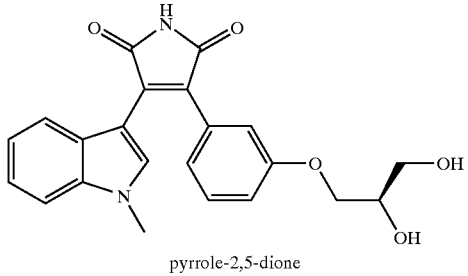

pyrrole-2,5-dione

Step 1

Toluenesulfonic acid (100 mg) was added to a solution of 3-(1-methylindol-3-yl)-4-[3-((R)-2,2-dimethyl-1,3-dioxolan-4-ylmethyloxy)phenyl]-1H-pyrrole-2,5-dione (4.3 g) in methanol (100 mL) and water (10 mL) and the reaction mixture was heated at 50° C. overnight. The volatiles were removed and the residue was partitioned between water and EtOAc. The organic layer was washed with NaCl (sat.) and dried over sodium sulfate. The crude product was purified on a silica gel column with 5% MeOH in CH₂Cl₂ and further purified by recrystallization from CH₂Cl₂/hexane to give 3-(1-methylindol-3-yl)-4-{3-[((R)-2-hydroxy-2-hydroxymethyl)ethyloxy]phenyl}-1H-pyrrole-2,5-dione (2.46 g). ¹H NMR (DMSO-d6): δ 11.05 (s, NH), 8.03 (s, 1H), 7.48 (d, 1H, J=8.2), 7.15 (m, 1H), 7.02 (s, 1H), 6.92 (m, 1H), 6.92 (m, 1H), 6.76 (t, 1H, J=7.3), 6.37 (t, 1H, J=8.0), 4.89 (d, OH, J=4.7), 4.61 (t, OH, J=5.8), 3.90 (s, 3H), 3.85 (m, 1H), 3.72 (m, 2H), 3.37 (m, 2H); MS (EI): M⁺ 392; m.p. 177.7–178.0° C.; Anal (C₂₂H₂₀N₂O₅-0.15H₂O): C, H, N.

Following the procedure described above but substituting 3-(1-methylindol-3-yl)-4-[3-((R)-2,2-dimethyl-1,3-dioxolan-4-ylmethyloxy)phenyl]-1H-pyrrole-2,5-dione with 3-(1-methylindol-3-yl)-4-[2-((R)-2,2-dimethyl-1,3-dioxolan-4-ylmethyloxy)phenyl]-1H-pyrrole-2,5-dione gave 3-(1-methylindol-3-yl)-4-{2-[(-2-hydroxy-2-hydroxymethyl)ethyloxy]-phenyl}-1H-pyrrole-2,5-dione.

$^1$H NMR (DMSO-d6): δ 10.96 (s, NH), 7.98 (s, 1H), 7.47 (d, 1H, J=8.1), 7.36 (t, 1H, J=8.8), 7.23 (d, 1H, J=7.2), 7.11 (t, 1H, J=7.1), 6.95 (m, 2H), 6.66 (t, 1H, J=7.3), 6.33 (d, 1H, J=8.0), 3.87 (s, 3H), 3.6 (br.s. 1H), 3.2 (br.s. 2H), 3.1 (br.s. 2H); m.p. 245.0–247.1° C.; MS (EI): M$^+$ 392; Anal ($C_{22}H_{20}O_5N_2$-1.20$H_2O$): C, N, H.

Following the procedure described above but substituting 3-(1-methylindol-3-yl)-4-[3-((R)-2,2-dimethyl-1,3-dioxolan-4-ylmethyloxy)phenyl]-1H-pyrrole-2,5-dione with 3-(1-methylindol-3-yl)-4-[4-((R)-2,2-dimethyl-1,3-dioxolan-4-ylmethyloxy)phenyl]-1H-pyrrole-2,5-dione gave 3-(1-methylindol-3-yl)-4-{4-[((R)-2-hydroxy-2-hydroxymethyl)ethyloxy]-phenyl}-1H-pyrrole-2,5-dione. $^1$H NMR (DMSO-d$_6$): δ 11.00 (s, NH), 7.97 (s, 1H), 7.48 (t, 1H, J=8.2), 7.34 (d, 2H, J=8.9), 7.13 (t, 1H, J=7.2), 6.87 (d, 2H, J=8.9), 6.86 (t, 1H, J=7.2), 6.43 (d, 1H, J=8.1), 4.00 (m, 11H), 3.90 (s, 3H), 3.8 (m, 2H), 3.43 (m, 2H); m.p. 220.3–222.7° C.; MS (EI): M$^+$ 392.

Following the procedure described above, but substituting 3-(1-methylindol-3-yl)-4-[3-((R)-2,2-dimethyl-1,3-dioxolan-4-ylmethyloxy)phenyl]-1H-pyrrole-2,5-dione with 3-(1-methylindol-3-yl)-4-{3-((S)-2,2-dimethyl-1,3-dioxolan-4-ylmethyloxy)phenyl]-1H-pyrrole-2,5-dione gave 3-(1-methylindol-3-yl)-4-{3-[((S)-2-hydroxy-2-hydroxymethyl)ethyloxy]-phenyl}-1H-pyrrole-2,5-dione. MS (EI): M$^+$ 392; m.p. 176.9–178.1° C.

Example 3

Synthesis of 3-(1-methylindol-3-yl)-4-[3-(2-morpholin-4-ylethyloxy)phenyl]-1H-pyrrole-2,5-dione

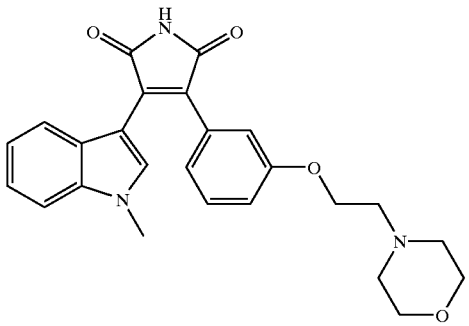

Step 1

To a stirred solution of 3-iodophenol (2.2 g, 10 mmol), N-(2-hydroxyethyl)morpholine (2 eq. 2.4 mL) and Ph$_3$P (2 eq. 5.24 g) in THF (90 mL) at 0° C. was added dropwise a solution of diisopropylazodicarboxylate (2 eq. 3.96 g) in THF (20 mL). The resulting solution was stirred at room temperature overnight and was then quenched with NaHCO$_3$. The product was extracted with EtOAc and the EtOAc layer was washed with NaCl (sat.), dried over sodium sulfate. The crude mixture was then purified on a silica gel column with 25% acetone in hexane to give 3-(2-morpholin-4-ylethyloxy)iodobenzene (2.8 g, 84% yield).

Step 2

A flask charged with 3-(2-morpholin-4-ylethyloxy)iodobenzene (0.33 g, 1 mmol), bis(pinacolato)diboron (0.279 g, 1.1 mmol), potassium acetate (0.294 g, 3 mmol) and PdCl$_2$(dppf) (48 mg, 0.06 mmol) was flushed with nitrogen. N,N-Dimethylformamide (6 mL) was added and the reaction mixture was stirred at 80° C. for 3h and then cooled to room temperature. 3-Bromo-4-(1-methylindol-3-yl)-1-methylpyrrole-2,5-dione (0.255 g, 0.8 mmol) ((synthesized according to the procedures described in Brenner, M. et al., *Tet. Lett.* 44, 2887, (1988)) was added to the reaction mixture, followed by the addition of PdCl$_2$ (dppf) (48 mg, 0.06 mmol)) and 2M aq. Na$_2$CO$_3$ (2.5 mL). The resulting mixture was stirred at 80° C. for 2.5 h, then cooled to room temperature, and quenched with H$_2$O. The product was extracted with EtOAc. The EtOAc layer was washed with H$_2$O, NaCl (sat.), dried over Na$_2$SO$_4$, and concentrated. Purification of the crude product on a silica gel column with 2/3/5 of acetone/CH$_2$Cl$_2$/hexane gave 3-(1-methylindol-3-yl)-4-[3-(2-morpholin-4-ylethyloxy)-phenyl]-1-methylpyrrole-2,5-dione as an orange-red oil. (0.25 g, 70% yield).

Step 3

3-(1-Methylindol-3-yl)-4-[3-(2-morpholin-4-ylethyloxy)phenyl]-1-methylpyrrole-2,5-dione (0.22 g, 0.5 mmol) was dissolved in EtOH (10 mL) and a solution of KOH (1.5 g) in H$_2$O (2.5 mL) was added. After the reaction mixture was refluxed for 3 h, it was cooled to room temperature, followed by evaporation of EtOH. The residue was acidified with aq. HCl to pH=4.5. The product was extracted with EtOAc and the EtOAc layer was dried over sodium sulfate and concentrated to give 3-(1-methylindol-3-yl)-4-[3-(2-morpholin-4-ylethyloxy)phenyl]furan-2,5-dione which was in the next step without further purification.

Step 4

3-(1-Methylindol-3-yl)-4-[3-(2-morpholin-4-ylethyloxy)phenyl]furan-2,5-dione was then dissolved in DMF (5 mL) and ammonium hydroxide (10 mL) was added. The resulting mixture was heated at 140° C. for 4 h, then cooled to room temperature, and diluted with water. The product was extracted into EtOAc. The EtOAc layer was washed with NaCl (sat.) and dried over sodium sulfate. Purificaiton on a silica gel column with 5% (10% NH$_4$OH in MeOH) in CH$_2$Cl$_2$ gave 3-(1-methylindol-3-yl)4-[3-(2-morpholin-4-ylethyloxy)phenyl]-1H-pyrrole-2,5-dione (0.21 g, >99% yield).

$^1$H NMR (CDCl$_3$): δ 7.95 (s, 1H), 7.41 (br.s. NH), 7.32 (d, 1H, J=7.2), 7.17 (m, 3H), 7.02 (s, 1H), 6.91 (d, 1H, J=6.5), 6.83 (t, 1H, J=7.1), 6.40 (d, 1H, J=8.1), 3.92 (br.s. 2H), 3.90 (s, 3H), 3.78 (br.s. 4H), 2.65 (br.s. 2H), 2.51 (br.s. 4H); MS (EI): M$^+$ 431; Anal ($C_{25}H_{25}O_4N_3$-0.3$H_2O$): C, H, N.

Following the procedure described above, but substituting 3-bromo-4-(1-methylindol-3-yl)-1-methylpyrrole-2,5-dione with 3-bromo-4-(1H-indol-3-yl)-1-methylpyrrole-2,5-dione, provided 3-(1H-indol-3-yl)-4-[3-(2-morpholin-4-ylethoxy)phenyl]-1H-pyrrole-2,5-dione. MS (EI): M$^+$ 417.

Example 4

Synthesis of 3-(1-methylindol-3-yl)-4-(3-morpholin-4-ylphenyl)-1H-pyrrole-2,5-dione

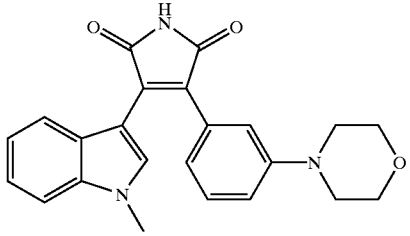

Step 1

A round bottom flasked flushed with argon was charged with methyl 3-bromophenyl-acetate (2.29 g, 10 mmol) (prepared from 3-bromophenylacetic acid as described in example 2, step 1), morpholine (1.05 mL, 1.2 eq.), CsCO$_3$ (4.55 g, 1.4 eq.), Pd$_2$(dba)$_3$ (92 mg, 0.01 eq) and BINAP (93 mg, 0.15 eq.) in toluene (20 mL). The resulting mixture was heated at 100° C. overnight and then diluted with diethyl ether (120 mL). The precipitates were filtered through a Celite pad and the filtrate was concentrated and purified on a silica-gel column with 20% EtOAc in hexane to give methyl 3-(morpholin-4-yl)phenylacetate (0.55 g, 23%).

Step 2

To a solution of methyl 3-(morpholin-4-yl)phenylacetate (0.50 g, 2.1 mmol) in methanol (5 mL) and H$_2$O (1 mL) was added lithium hydroxide monohydrate (0.18 g, 2 eq.). After the reaction mixture was stirred at room temperature overnight, it was concentrated to dryness. Acetic acid was then added to the residue and the resulting mixture was partitioned between EtOAc and H$_2$O. The organic layer was washed with NaCl (sat.), dried over Na$_2$SO$_4$, and evaporation under vacuo to give 3-(morpholin-4-yl)phenylacetic acid (0.42 g).

Step 3

3-(Morpholin-4-yl)phenylacetic acid (0.42 g, 1.9 mmol) was dissolved in CH$_2$Cl$_2$ (5 mL) and oxalyl chloride (0.22 mL, 1.2 eq.) was added. The reaction mixture was stirred at room temperature for 2 h and then cooled to 0° C. Ammonium hydroxide solution (2 mL) was added dropwise. Volatiles were removed and the crude mixture was dissolved in methanol, stirred, and filtered. The filtrate was concentrated to give 3-(morpholin-4-yl)benzylamide (0.5 g) which was in the next step without any further purification).

Step 4

To a suspension of 3-(morpholin-4-yl)benzylamide (0.5 g) and methyl indoleglyoxalate (0.55 g, 2.5 mmol) in THF at 0° C. was added potassium tert-butoxide (1.0 M, 3.45 mL, 3.45 mmol) dropwise. The reaction mixture which turned orange in color was stirred at 0° C. for 1 h and then allowed to warm to room temperature. After stirring overnight, the reaction mixture was quenched with H$_2$O and extracted with EtOAc. The organic layer was washed with NaCl (sat.), and dried over Na$_2$SO$_4$. Preparative TLC purificaiton with 5% MeOH in CH$_2$Cl$_2$ gave 3-(1-methylindol-3-yl)-4-(3-morpholin-4-ylphenyl)-1H-pyrrole-2,5-dione (150 mg) as an oil which was converted to the hydrochloride salt and recrystallized from EtOAc to give 3-(1-methylindol-3-yl)-4-(3-morpholin-4-ylphenyl)-1H-pyrrole-2,5-dione hydrochloride (72 mg) as a solid.

$^1$H NMR (DMSO-d6): δ 11.02 (s, NH), 8.02 (s, 1H), 7.48 (d, 1H, J=8.1), 7.15 (m, 2H), 6.90 (m, 2H), 6.74 (t, 1H, J=7.4), 6.34 (d, 1H, J=8.1), 3.90 (s, 3H), 3.62 (m, 4H), 2.8 (m, 4H); MS (LSIMS): (M+H)$^+$ 388.

Following the procedure described above, but substituting morpholine with pyrrolidine in Step 1, 3-(1-methylindol-3-yl)-4-(3-pyrrolidin-1-ylphenyl)-1H-pyrrole-2,5-dione was prepared. MS (EI): M$^+$ 372.

Example 5

Synthesis of 3-(1-methylindol-3-yl)-4-[3-(3-aminopropyloxy)phenyl]-1H-pyrrole-2,5-dione

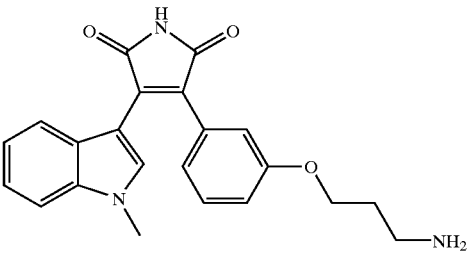

Step 1

To a solution of methyl 3-hydroxyphenyl acetate (2.49 g, 15 mmol) and 1-bromo-3-chloropropane (2.96 mL, 2eq.) in acetonitrile (50 mL) was added cesium carbonate (5.4 g, 1.1 eq.). The reaction mixture was refluxed for 24 h, then cooled to room temperature and filtered through a Celite pad. The filtrate was concentrated and the residue was purified on a silica gel column with 5/55/40 of MeOH/CH$_2$Cl$_2$/hexane to give methyl 3-(3-chloro-propyloxy)phenyl acetate (4.2 g) as an oil.

Step 2

To a solution of methyl 3-(3-chloropropyloxy)phenyl acetate (2.87 g, 10 mmol) in methanol (15 mL) was added LiOH-H$_2$O (0.84 g, 2 eq.). The reaction mixture was stirred at room temperature for 2 h. Volatiles were removed and the residue was partitioned between EtOAc and water. The aqueous layer was acidified and extracted with EtOAc. The combined EtOAc layers were washed with NaCl (sat.), dried over Na$_2$SO$_4$ and concentrated to give 3-(3-chloropropyloxy)phenylacetic acid (2.8 g).

Step 3

To a solution of N-methylindole (1.16 mL, 9.1 mmol) in diethyl ether (70 mL) at 0° C. was added dropwise oxalyl chloride (0.83 mL, 1.1 eq.). After the additon, the reaction mixture was stirred at 0° C. for 15 min., and the volatiles were removed under vacuo. The residue was re-dissolved in dichloromethane (70 mL) and triethylamine (2.3 mL, 2 eq.) was added. The reaction mixture was cooled to 0° C. and a solution of 3-(3-chloro-propyloxy)phenylacetic acid (2.73 g, 10 mmol) in dichloromethane (70 mL) was added dropwise. The resulting mixture was stirred at 0° C., and then allowed to warm up to room temperature overnight. Volatiles were removed under vacuo and the residue was purified on a silica gel column with dichloromethane to give 3-(1-methylindol-3-yl)-4-[3-(3-chloropropyloxy)phenyl]furan-2,5-dione (1.1 g).

Step 4

To a solution of 3-(1-methylindol-3-yl)-4-[3-(3-chloropropyloxy)phenyl]furan-2,5-dione (1.0 g, 2.2 mmol) in DMF (15 mL) was added sodium azide (0.43 g, 3 eq.) and the resulting mixture was heated at 75° C. for 24 h. The reaction mixture was cooled to room temperature and quenched with water. The product was then extracted into EtOAc. The EtOAc layer was washed with H$_2$O, NaCl (sat.), dried over Na$_2$SO$_4$, and concentrated in vacuo to give 3-(1-methylindol-3-yl)-4-[3-(3-azidopropyloxy)phenyl]furan-2,5-dione (1.0 g) which was used directly in the next step without any further purification.

Step 5

To a solution of 3-(1-methylindol-3-yl)-4-[3-(3-azidopropyloxy)phenyl]furan-2,5-dione (1.0 g) in DMF (7 mL) was added and ammonium hydroxide (50 mL). The reaction mixture was heated at 140° C. for 3.5 h, then cooled to room temperature and diluted with water. The precipitates were filtered and dried to give 3-(1-methylindol-3-yl)-4-[3-(3-azidopropyloxy)phenyl]-1H-pyrrole-2,5-dione (0.58 g). MS (EI): M$^+$ 401.

Step 6

To a solution of 3-(1-methylindol-3-yl)-4-[3-(3-azidopropyloxy)phenyl]-1H-pyrrole-2,5-dione (0.4 g, 1 mmol) in THF (20 mL) was added Ph$_3$P (0.25 g, 1.1 eq.), followed by the H$_2$O (0.017 mL). The resulting mixture was stirred at room temperature for 48 h and then concentrated in vacuo. The residue was purified on a silica gel column with 8% (10% NH$_4$OH in methanol) in CH$_2$Cl$_2$ to give 3-(1-methylindol-3-yl)-4-[3-(3-aminopropyloxy)-phenyl]-1H-pyrrole-2,5-dione (0.35 g) which was converted to HCl salt and recrystalized to give 3-(1-methylindol-3-yl)-4-[3-(3-aminopropyloxy)phenyl]-1H-pyrrole-2,5-dione (0.21 g) as the HCl salt.

1H NMR (DMSO-d6): δ 11.1 (s, NH), 8.06 (s, 1H), 7.50 (d, 1H, J=8.2), 7.20 (m, 2H), 6.91 (m, 2H), 6.73 (t, 1H, J=7.2), 6.33 (d, 1H, J=8.0), 3.93 (m, 2H), 3.91 (s, 3H), 3.67 (br.s. 2H), 1.85 (m, 2H); MS (EI): M$^+$ 375.

Example 6

Synthesis of 3-(1-methylindol-3-yl)-4-[3-(2-aminoethyloxy)phenyl]-1H-pyrrole-2,5-dione

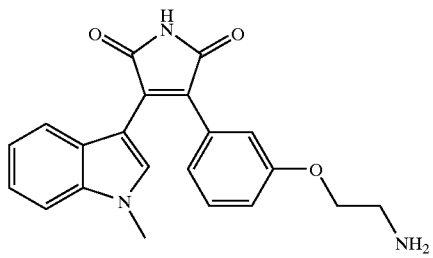

Step 1

To a stirred solution of methyl 3-hydroxyphenylacetate (1.66 g, 10 mmol), 2-chloroethanol (1.34 mL, 2 eq.) and triphenylphosphine (5.24 g, 2 eq.) in THF (100 mL) at 0° C. was added dropwise diisopropylazodicarboxylate (3.96 mL, 2 eq.) and the resulting mixture was stirred at room temperature overnight. The reaction mixture was then quenched with NaHCO$_3$ and the product was extracted with EtOAc. The EtOAc layers were washed with brinebrine, dried over sodium sulfate, and concentrated. Purification on a silica gel column with 10% EtOAc in hexane gave methyl 3-(2-chloroethyloxy)phenylacetate (1.6 g, 70% yield) which was converted to 3-(1-methylindol-3-yl)-4-[3-(2-aminoethyloxy)phenyl]-1H-pyrrole-2,5-dione by following the procedure described in Example 5, Steps 2–6 above.

$^1$H NMR (DMSO-d6): δ 11.11 (s, NH), 8.22 (br.s. NH2), 8.05 (s, 1H), 7.49 (d, 1H, J=8.2), 7.20 (m, 1H), 7.12 (s, 1H), 6.99 (dd, 1H, J=2.6, 8.3), 6.90 (d, 1H, J=7.8), 6.75 (t, 1H, J=7.3), 6.35 (d, 1H, J=8.1), 4.09 (t, 2H, J=5.0), 3.91 (s, 3H), 3.15 (br.s. 2H); MS (LSIMS): (M+H)$^+$ 362; Anal (C$_{21}$H$_{20}$N$_3$O$_3$Cl·0.85H$_2$O): C, H, N.

Example 7

Synthesis of 3-(1-methylindol-3-yl)-4-{3-[(2-(RS)-hydroxy-2-hydroxymethyl)ethylamino]phenyl}-1H-pyrrole-2,5-dione

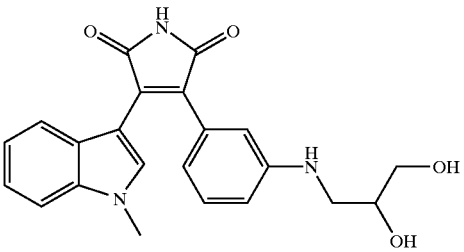

Step 1

Oxalyl chloride (4.9 mL, 56 mmol) was added dropwise to a stirred solution of 1-methylindole (6.5 mL, 51 mmol) in ether (350 mL) at 0° C. After the completion of the addition, the reaction mixture was stirred at 0° C. for 30 min., and then the volatiles were removed under reduced pressure to afford 1-methylindole-3-glyoxylyl chloride.

Step 2

A solution of 1-methylindole-3-glyoxylyl chloride in dichloromethane (350 mL) was added to a solution of 3-nitrophenylacetic acid (8.5 g, 0.093 mL) and triethylamine (13 mL, 93 mmol) in dichloromethane (350 mL) at 0° C. The reaction mixture was then stirred at room temperature overnight and then concentrate under reduced pressure. The crude product was purified on a silica gel column with 6:1 hexane/ethyl acetate to afford 3-(1-methylindol-3-yl)-4-(3-nitrophenyl)furan-2,5-dione (9 g, 55%).

Step 3

A solution of 3-(1-methylindol-3-yl)-4-(3-nitrophenyl)furan-2,5-dione (9 g, 26 mmol) in DMF (20 mL) was heated to about 140° C. Aqueous ammonia (20 mL) was added in portions and the heating was continued for 6 h. Water (20 mL) was added and the reaction mixture was allowed to stand at room temperature overnight. The orange colored solid was filtered off, washed with water and dried under vacuum to afford 3-(1-methylindol-3-yl)-4-(3-nitrophenyl)-1H-pyrrole-2,5-dione (6.7 g, 75%).

Step 4

To a solution of 3-(1-methylindol-3-yl)-4-(3-nitrophenyl)-1H-pyrrole-2,5-dione (6.5 g, 19 mmol) in acetone (500 mL), was added TiCl$_3$ (45 mL) in 5 portions at 30 minute interval. The reaction mixture was stirred at room temperature overnight and then neuteralized with 10N NaOH. The product was extracted with EtOAc, dried, and concentrated. The crude product was purified on a silica gel column with 3% MeOH in CH$_2$Cl$_2$ to afford 3-(1-methylindol-3-yl)-4-(3-aminophenyl)-1H-pyrrole-2,5-dione (4.9 g, 82.5%).

Step 5

A mixture of 3-(1-methylindol-3-yl)-4-(3-aminophenyl)-1H-pyrrole-2,5-dione (100 mg, 0.32 mmol) and 2,2-dimethyldioxolane-4-carboxaldehyde (0.38 mmol) (prepared as described in Kumont, von R., et al. *Helv. Chim. Acta.*, 66, 814, (1983)) in dichloromethane (12 mL) was stirred at room temperature for 10 min., and then Na(OAc)$_3$BH (120 mg, 0.57 mmol) was added. The reaction mixture was stirred overnight and then partition between EtOAc and H$_2$0. The organic layer was separated, washed with water and concentrated. The crude product was purified by preparatory TLC with 3/1 hexanes/EtOAc to give 3-(1-methylindol-3-yl)-4-[3-(2,2-dimethyldioxolan-4-ylmethylamino)phenyl]-1H-pyrrole-2,5-dione (32.6 mg, 24%).

Step 6

3-(1-Methylindol-3-yl)-4-[3-(2,2-dimethyldioxolan-4-ylmethylamino)phenyl]-1H-pyrrole-2,5-dione (30 mg) was dissolved in MeOH (5 mL) and $H_2O$ (1 mL). Catalytic amount of p-toluenesulfonic acid was added and the reaction mixture was stirred at 50° C. overnight. The reaction mixture was concentrate and the residue was purified by preparatory TLC to give 3-(1-methylindol-3-yl)-4-{3-[(2-(RS)-hydroxy-2-hydroxymethyl)ethylamino]phenyl}-1H-pyrrole-2,5-dione (18 mg, 66%). MS(EI): $M^+$ 391

Example 8

Synthesis of 3-(1-methylindol-3-yl)-4-(3-tetrahydropyran-4-ylaminophenyl)-1H-pyrrole-2,5-dione

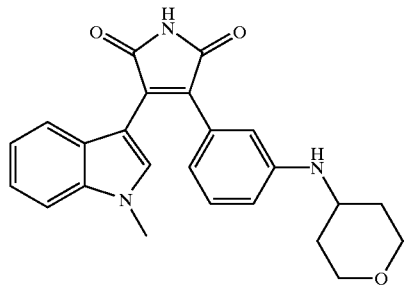

A mixture of 3-(1-methylindol-3-yl)-4-(3-aminophenyl)-1H-pyrrole-2,5-dione (100 mg, 0.32 mmol) and tetrahydro-4H-pyran-4-one (65 mg, 0.65 mmol) in MeOH (8 mL) was stirred at room temperature for 40 min., and then $NaCNBH_3$ (63 mg, 1.0 mmol) was added. After stirring the reaction mixture overnight the volatiles were removed under vacuo and the residue was purified by preparatory TLC (3% $MeOH/CH_2Cl_2$) to give 3-(1-methylindol-3-yl)-4-(3-tetrahydropyran-4-ylaminophenyl)-1H-pyrrole-2,5-dione (88.2 mg, 70%). LC/MS: $M^+$ 401(98.6%).

Example 9

Synthesis of 3-(1-methylindol-3-yl)-4-[3-(2,2-dimethyl-1,3-dioxan-5-ylamino)phenyl]-1H-pyrrole-2,5-dione

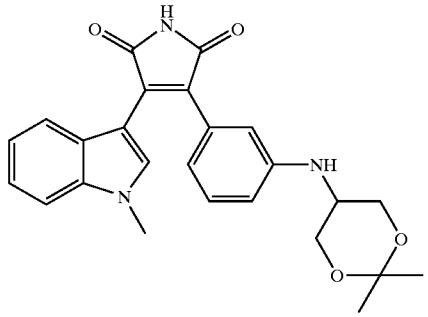

A mixture of 3-(1-methylindol-3-yl)-4-(3-aminophenyl)-1H-pyrrole-2,5-dione (200 mg, 0.63 mmol) and 2,2-dimethyl-1,3-dioxane-5-one (98 mg, 0.76 mmol) in MeOH (10 mL) was stirred at room temperature for 15 min., and then $NaCNBH_3$ (79 mg, 1.26 mmol) was added. After stirring the reaction mixture overnight the volatiles were removed under vacuo and the residue was purified by preparatory TLC (1% $MeOH/CH_2Cl_2$) to give 3-(1-methylindol-3-yl)-4-[3-(2,2-dimethyl-1,3-dioxan-5-ylamino)phenyl]-1H-pyrrole-2,5-dione (185 mg, 68%). MS(EI): $M^+$ 431, MP: 201–203° C.

Example 10

Synthesis of 3-(1-methylindol-3-yl)-4-[3-(1-(RS)-hydroxy-2-hydroxymethylethylamino)phenyl]-1H-pyrrole-2,5-dione

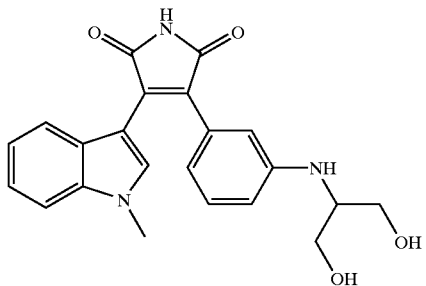

A solution of 3-(1-methylindol-3-yl)-4-[3-(2,2-dimethyl-1,3-dioxan-5-yl-amino)phenyl]-1H-pyrrole-2,5-dione (173 mg, 0.4 mmol) in MeOH (30 mL) and $H_2O$ (3 mL) with catalytic amount of p-toluenesulfonic acid was stirred at 500° C. overnight. The volatiles were removed under vacuo and the residue was purified by preparatory TLC (3% $MeOH/CH_2Cl_2$) to afford 3-(1-methylindol-3-yl)-4-[3-(1-(RS)-hydroxy-2-hydroxymethylethylamino)phenyl]-1H-pyrrole-2,5-dione (130 mg, 83%). MS(LSIMS): $(M+H)^+$ 392, MP: 97.5–101° C.

Example 11

Synthesis of 3-(1-methylindol-3-yl)-4-[3-(imidazol-2-ylmethylamino)phenyl]-1H-pyrrole-2,5-dione

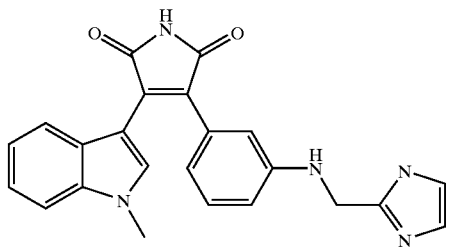

A mixture of 3-(1-methylindol-3-yl)-4-(3-aminophenyl)-1H-pyrrole-2,5-dione (100 mg, 0.32 mmol) and imidazole-2-carboxaldehyde (40 mg, 0.42 mmol) in MeOH (8 mL) was stirred for 15 min., and then $NaCNBH_3$ (40.2 mg, 0.64 mmol) was added. After stirring the reaction mixture overnight the volatiles were removed under vacuo and the residue was purified by preparatory TLC (3% $MeOH/CH_2Cl_2$) to afford 3-(1-methylindol-3-yl)-4-[3-(imidazol-2-ylmethylamino)phenyl]-1H-pyrrole-2,5-dione (24.8 mg, 20%). LC/MS: $M^+$ 397(94.2%).

Example 12

Synthesis of 3-(1-methylindol-3-yl)-4-[3-(3-tert-butyldimethylsilyloxypropylamino)phenyl]-1H-pyrrole-2,5-dione

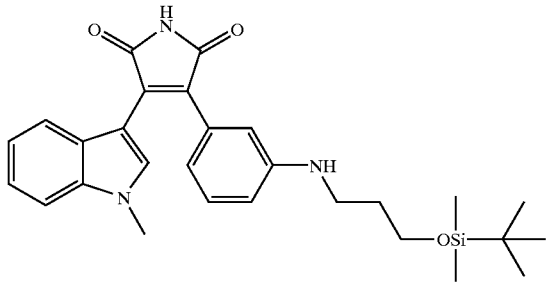

Step 1

Tetrapropylammonium perruthenate (0.18 g, 5.3 mmol) was added to a mixture of methylene chloride (20 mL) and acetonitrile (2 mL) containing 3-(tert-butyldimethylsilyloxy)-propanol (2 g, 0.01 mmol), N-methylmorpholine N-oxide (1.76 g) and 4 Å molecular sieves. The reaction mixture was stirred at RT overnight and then filtered through a pad of silica gel. The filtrate was concentrated under vacuo to afford 3-(tert-butyldimethylsilyloxy)-propionaldehyde (1.3 g, 66%).

Step 2

A mixture of 3-(1-methylindol-3-yl)-4-(3-aminophenyl)-1H-pyrrole-2,5-dione (0.2 g, 6 mmol) and 3-(tert-butyldimethylsilyloxy)propionaldehyde (0.25 g, 13 mmol) in $CH_2Cl_2$ (10 mL) and MeOH (5 mL) was stirred at room temperature for 15 min and then $NaCNBH_3$ (57 mg, 1.5 eq) was added. The reaction mixture was stirred at RT overnight and then concentrated under vacuo. The residue was purified by preparatory TLC to give 98 mg 3-(1-methylindol-3-yl)-4-[3-(3-tert-butyldimethylsilyloxypropylamino)phenyl]-1H-pyrrole-2,5-dione (32%) MS (LSIMS): $(M+H)^+$ 490, MP: 58–65° C.

Proceeding as described in example 12 above, but substituting 3-(tert-butyldimethylsilyloxy)propanol with 2-(tert-butyldiphenylsilyloxy)ethanol provided 3-(1-methylindol-3-yl)-4-[3-(3-tert-butyldiphenylsilyloxy-ethylamino)phenyl]-1H-pyrrole-2,5-dione.

Example 13

Synthesis of 3-(1-methylindol-3-yl)-4-[3-(3-hydroxypropylamino)phenyl]-1H-pyrrole-2,5-dione

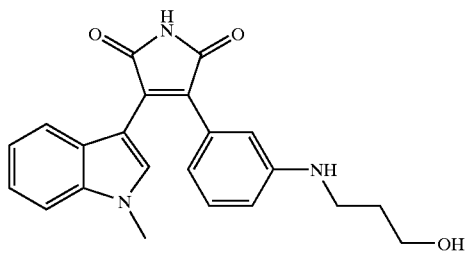

To a solution of 3-(1-methylindol-3-yl)-4-[3-(3-tert-butylsilyloxypropylamino)-phenyl]-1H-pyrrole-2,5-dione (85 mg, 0.17 mmol) in THF (3 mL) was added a solution of 1M tetrabutylammonium fluoride in THF (5 mL) via a syringe. The reaction mixture was stirred at room temperature for 1 h and then concentrated in vacuo. The residue was purified by preparatory TLC (4% $MeOH/CH_2Cl_2$) to give 3-(1-methylindol-3-yl)-4- [3-hydroxy-propylamino)phenyl]-1H-pyrrole-2,5-dione which was converted to HCl salt (29 mg, 41%) by dissolving it in MeOH and adding 1M HCl in ether (3 mL). MS(LSIMS): $(M+H)^+$ 376, MP: 180–192° C.

Proceeding as described in example 13 above, but substituting 3-(1-methylindol-3-yl)-4-[3-(3-tert-butylsilyloxypropylamino)-phenyl]-1H-pyrrole-2,5-dione with 3-(1-methylindol-3-yl)-4-[3-(3-tert-butyldiphenylsilyloxyethylamino)phenyl]-1H-pyrrole-2,5-dione provided 3-(1-methylindol-3-yl)4-[3-(2-hydroxyethylamino)phenyl]-1H-pyrrole-2,5-dione. MS(LSIMS): $(M+H)^+$ 362, MP: 170.3–170.6° C.

Example 14

Synthesis of 3-(1-methylindol-3-yl)-4-[3-(3-hydroxy-1-methylpropylamino)phenyl]-1H-pyrrole-2,5-dione

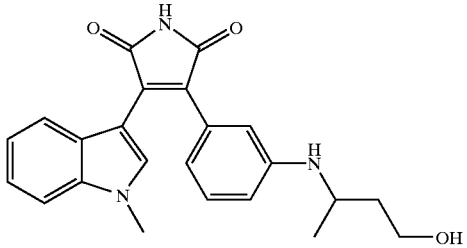

To a mixture of 3-(1-methylindol-3-yl)-4-(3-aminophenyl)-1H-pyrrole-2,5-dione (0.2 g, 0.6 mmol) and 4-hydroxy-2-butanone (80 mg, 1.5 eq) in dichloromethane (15 mL) was added $NaCNBH_3$ (56 mg, 1.5 eq) and the reaction mixture was stirred at RT for three days. The product 3-(1-methylindol-3-yl)-4-[3-(3-hydroxy-1-methylpropylamino)phenyl]-1H-pyrrole-2,5-dione separated by preparatory TLC (8.9 mg, 3.6%). LC/mS: $M^+$ 389.

Example 15

Synthesis of 3-(1-methylindol-3-yl)-4-[3-(2-hydroxy-1-methylethylamino)phenyl]-1H-pyrrole-2,5-dione

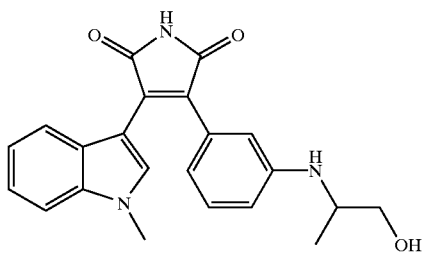

To a mixture of 3-(1-methylindol-3-yl)-4-(3-aminophenyl)-1H-pyrrole-2,5-dione (100 mg, 0.32 mmol) and hydroxyacetone (0.03 mL, 1.5 eq) in $CH_2Cl_2$ (12 mL) and THF (5 mL) was added $NaCNBH_3$ (28 mg, 1.5 eq) and the reaction mixture was stirred overnight. The volatiles were removed under vacuo and the residue was purified by preparatory TLC to give 3-(1-methylindol-3-yl)-4-[3-(2-hydroxy-1-methylethylamino)phenyl]-1H-pyrrole-2,5-dione (8 mg). LC/MS: $M^+$ 375(85.6%).

Example 16

Synthesis of 3-(1-methyl-5-chloroindol-3-yl)-4-{3-[((RS)-2,3-dihydroxypropylamino]phenyl}-1H-pyrrole-2,5-dione

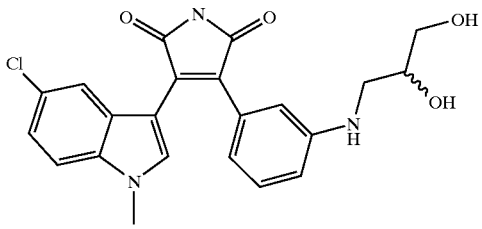

Step 1
To room temperature solution of 5-chloroindole (4.97 g) in dry DMF (40 mL) was added potassium hydroxide pellets (2.76 g) and stirred 1 h until most of the solid dissolved. The resulting mixture was cooled to 0° C. in an ice bath and iodomethane (2.45 mL) was added dropwise and later stirred overnight at room temperature under argon. The reaction mixture was poured into water and extracted twice with ETOAc. The combined ETOAc portions were combined, washed with water, dried over magnesium sulfate, concentrated, and flash chromatographed with 10% ETOAc/Hexane to give 1-methyl-5-chloroindole as a pink liquid (5.43 g).

Step 2
1-Methyl-5-chloroindole-3-glyoxylyl chloride was prepared by proceeding as described in Example 12, Step 1, but substituting 1-methyl-5-chloroindole for 1-methylindole.

Step 3
3-(1-Methyl-5-chloroindol-3-yl)-4-(3-nitrophenyl)furan-2,5-dione was prepared by proceeding as described in Example 12, Step 2, but substituting 1-methyl-5-chloroindole-3-glyoxylyl chloride for 1-methylindole-3-glyoxylyl chloride.

Step 4
3-(1-Methyl-5-chloroindol-3-yl)-4-(3-nitrophenyl)-1H-pyrrole-2,5-dione was prepared by proceeding as described in Example 12, Step 3, but substituting 3-(1-methyl-5-chloroindol-3-yl)-4-(3-nitrophenyl)furan-2,5-dione for 3-(1-methylindol-3-yl)-4-(3-nitrophenyl)furan-2,5-dione.

Step 5
A mixture of 3-(1-methyl-5-chloroindol-3-yl)-4-(3-nitrophenyl)-1H-pyrrole-2,5-dione (865 mg), 10% palladium on carbon (90 mg), and glacial HOAc (35 mL) was stirred and hydrogenated at atmospheric pressure using a balloon (2 h). The reaction mixture was filtered through a pad of celite, cooled to 0° C. and KOH pellets were added until pH 8. The solution was extracted with ETOAc, dried (magnesium sulfate), and stripped. The crude was flash chromatographed with 10% through 20% ETOAc-Hexane to provide 3-(1-methyl-5-chloroindol-3-yl)-4-(3-aminophenyl)-1H-pyrrole-2,5-dione (495 mg).

Step 6
To a room temperature solution of 3-(1-methyl-5-chloroindol-3-yl)-4-(3-aminophenyl)-1H-pyrrole-2,5-dione (492 mg) in methanol (250 mL) was added DL-glyceraldehyde dimer dissolved in water (15 mL) followed by sodium cyanoborohydride (110 mg) and the reaction mixture was stirred overnight under argon. The reaction appeared to be only 30% complete by TLC. Additional dimer (150 mg) and cyanoborohydride (100 mg) were added. After another 6 h, the reaction appeared to be 50% complete. The solvent was removed and the crude residue was flash chromatographed with 5% to 7% to 10% MeOH/dichloromethane. 3-(1-Methyl-5-chloroindol-3-yl)-4-{3-[((RS)-2,3-dihydroxypropylaminolphenyl}-1H-pyrrole-2,5-dione was obtained as a dark red solid (220 mg). MS(EI): (M+H)$^+$ 426. M. pt. 224.8–226.1° C.

Example 17

Synthesis of 3-(1-methyl-5-fluoroindol-3-yl)-4-{3-[((RS)-2,3-dihydroxypropylamino]phenyl}-1H-pyrrole-2,5-dione

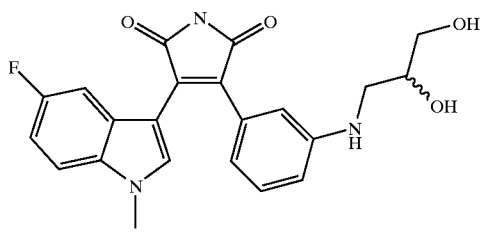

Step 1
1-Methyl-5-fluoroindole was prepared by proceeding as described in Example 16, Step 1, but substituting 5-fluoroindole for 5-chloroindole.

Step 2
1-Methyl-5-fluoroindole-3-glyoxylyl chloride was prepared by proceeding as described in Example 16, Step 2, but substituting 1-methyl-5-fluoroindole for 1-methyl-chloroindole.

Step 3
3-(1-Methyl-5-fluoroindol-3-yl)-4-(3-nitrophenyl)furan-2,5-dione was prepared by proceeding as described in Example 16, Step 3, but substituting 1-methyl-5-fluoroindole-3-glyoxylyl chloride for 1-methyl-5-chloroindole-3-glyoxylyl chloride.

Step 4
3-(1-Methyl-5-fluoroindol-3-yl)-4-(3-nitrophenyl)-1H-pyrrole-2,5-dione was prepared by proceeding as described in Example 16, Step 3, but substituting 3-(1-methyl-5-fluoroindol-3-yl)-4-(3-nitrophenyl)furan-2,5-dione for 3-(1-methyl-5-chloroindol-3-yl)-4-(3-nitrophenyl)furan-2,5-dione.

Step 5
3-(1-Methyl-5-fluoroindol-3-yl)-4-(3-aminophenyl)-1H-pyrrole-2,5-dione was prepared by proceeding as described in Example 16, Step 5, but substituting 3-(1-3-(1-methyl-5-fluoroindol-3-yl)-4-(3-nitrophenyl)-1H-pyrrole-2,5-dione for 1-methyl-5-chloroindol-3-yl)-4-(3-nitrophenyl)-1H-pyrrole-2,5-dione.

Step 6
3-(1-methyl-5-fluoroindol-3-yl)-4-{3-[((RS)-2,3-dihydroxypropylamino]phenyl}-1H-pyrrole-2,5-dione was prepared by proceeding as described in Example 16, Step 5, but substituting 3-(1-methyl-5-fluoroindol-3-yl)-4-(3-aminophenyl)-1H-pyrrole-2,5-dione for 3-(1-methyl-5-chloroindol-3-yl)-4-(3-aminophenyl)-1H-pyrrole-2,5-dione. MS(EI) (M+H)$^+$ 410, MP: 223.2°–225°.

Example 18

Synthesis of 3-(1-methylindol-3-yl)-4-[3-((R)-2,2-dimethyl-1,3-dioxolan-4-ylmethylsulfanyl)phenyl]-1H-pyrrole-2,5-dione

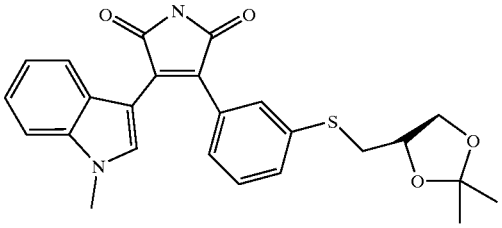

Step 1

To a cold methanol (20 mL) at 0° C. was added thionyl chloride (7 mL) dropwise. After the completion of the addition, the reaction mixture was stirred at 0° C. for 10 min, and was then added 3-mercaptophenylacetic acid (4.0 g, 23.8 mmol). The resulting mixture was stirred at room temperature overnight. Volatiles were removed and the residue was partitioned between water and ethyl acetate. The organic layer was separated, washed with $H_2O$, $NaHCO_3$, and NaCl (sat.) and dried over $Na_2SO_4$. The crude product was purified on a silica gel column with 20% EtOAc in hexane to give bis(3-ethoxycarbonylmethylphenyl)-disulfide (4.1 g).

Step 2

To a solution of bis(3-methoxycarbonylmethylphenyl) disulfide (4.1 g, 11 mmol) in THF (20 mL) and methanol (5 mL) was added $NaBH_4$ (1.76 g, 4 eq.) and the resulting mixture was stirred at RT overnight. It was then quenched with $NH_4Cl$ (sat.) and extracted with EtOAc. The EtOAc layer was washed with water, NaCl (sat.) and dried over $Na_2SO_4$. Column purificaton with 15% EtOAc in hexane gave 3.47 g of methyl (3-mercaptophenyl)acetate (84%).

Step 3

To a solution of methyl (3-mercaptophenyl)acetate (3.47 g, 19 mmol) in N-methylpyrrolidinone (100 mL) were added (R)-2,2-dimethyl-1,3-dioxolan-4-ylmethyl p-tosylate) (6.54 g, 1.2 eq.) and $K_2CO_3$ (7.9 g, 4 eq.). The reaction mixture was heated at 65° C. overnight. It was cooled to room temperature, quenched with water and extracted with EtOAc. The organic layer was separated, washed with water and NaCl (sat.), and dried over $Na_2SO_4$. The crude product was purified on a silica gel column with 10% EtOAc in hexane to give 5.2 g of methyl 3-(R)-2,2-dimethyl-1,3-dioxolan-4-ylmethylsulfanyl)phenylacetate (92%).

Step 4

Oxalyl chloride (1.05 eq., 3.64 mL) was added dropwise to a solution of N-methylindole (5.1 mL, 50 mmol) in diethyl ether (395 mL) at 0° C. Yellow precipitates were formed. After the completion of the addition, the reaction mixture was stirred at 0° C. for 30 min. The suspension was then dropwise added to a solution of 100 mL of ammonium hydroxide at 0° C. White precipitate was formed and the reaction mixture was stirred at 0° C. for 10 min., after the completion of addition. Dichloromethane was added to extract and the organic layer was separated, washed with NaCl (sat.), dried over sodium sulfate and concentrated. The residue was recrystallized from dichloromethane and hexane to give 5.6 g of N-methylindolyl-3-glyoxylamide.

Step 5

To a solution of N-methylindolyl-3-glyoxylamide (0.404 g, 2 mmol) in THF (15 mL) at 0° C. was added potassium tert-butoxide (2 mL, 1.0 M in THF) dropwise. Precipitate was formed and the reaction mixture was stirred at 0° C. for 5 min. Methyl 3-(R)-2,2-dimethyl-1,3-dioxolan-4-ylmethylsulfanyl)phenylacetate (0.65 g, 1.1 eq.) was then added, stirred for 5 min., and was followed by the addition of potassium tert-butoxide (4 mL, 1.0 M). The resulting mixture was stirred at 0° C. for 2 h and was allowed to warm to rt. After 3 h, methyl 3-(R)-2,2-dimethyl-1,3-dioxolan-4-ylmethylsulfanyl)phenylacetate (0.65 g) was added and the reaction mixture was stirred at rt overnight. It was then quenched with ammonium chloride (sat.) and extracted with EtOAc. The organic layer was washed with NaCl (sat.), dried and concentrated. Column purification with 7/43/50 of EtOAc/$CH_2Cl_2$/hexanes gave 0.52 g of 3-(1-methylindol-3-yl)-4-[3-(R)-2,2-dimethyl-1,3-dioxolan-4-ylmethylsulfanyl)-phenyl]-1H-pyrrole-2,5-dione. MS(EI): $M^+$ 448.

Example 19

Synthesis of 3-(1-methylindol-3-yl)-4-[3-((R)-2,2-dimethyl-1,3-dioxolan-4-ylmethylsulfinyl)phenyl]-1H-pyrrole-2,5-dione

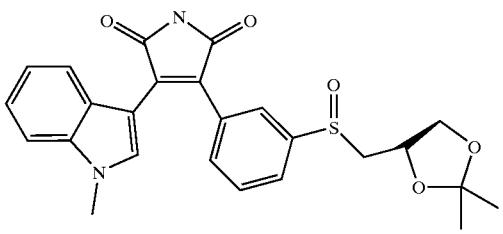

To a solution of 3-(1-methylindol-3-yl)-4-[3-(R)-2,2-dimethyl-1,3-dioxolan-4-ylmethylsulfanyl)phenyl]-1H-pyrrole-2,5-dione (100 mg, 0.22 mmol) in methanol (5 mL) and water (2.5 mL) at −10° C. was added oxone (16 mg, 1.15 eq.) and stirred for 2 h at −10° C. The reaction mixture was then poured into ice water and extracted with dichloromethane. The organic layer was washed with $NaS_2O_3$ (15% aq.), NaCl (sat.) and dried over sodium sulfate. Preparative TLC with 2/4/4 of acetone/dichloromethane/hexane gave 45 mg of 3-(1-methylindol-3-yl)-4-[3-((R)-2,2-dimethyl-1,3-dioxolan-4-ylmethylsulfinyl)phenyl]-1H-pyrrole-2,5-dione. MS (ESI): $(M+H)^+$ 465.

Example 20

Synthesis of 3-(1-methylindol-3-yl)-4-[3-((R)-2,2-dimethyl-1,3-dioxolan-4-ylmethylsulfonyl)phenyl]-1H-pyrrole-2,5-dione

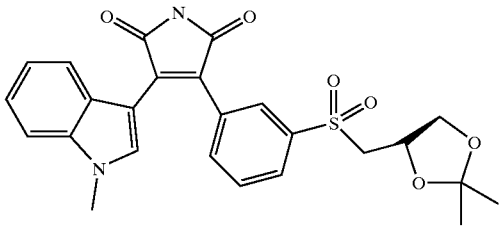

To a solution of 3-(1-methylindol-3-yl)-4-[3-((R)-2,2-dimethyl-1,3-dioxolan-4-ylmethylsulfanyl)phenyl]-1H-pyrrole-2,5-dione (100 mg, 0.22 mmol) in methanol (20 mL) and water (5 mL) was added oxone in 5 mL of water at 0° C. The resulting suspension was stirred at 0° C. for 30 min., and was allowed to warm to rt and stirred for 5 h. The reaction mixture was then poured into ice water and extracted with dichloromethane. The organic layer was washed with NaS$_2$O$_3$ (15% aq.), NaCl (sat.) and dried over sodium sulfate. Preparative TLC with 2/4/4 of acetone/dichloromethane/hexane gave 40 mg of 3-(1-methylindol-3-yl)-4-[3-((R)-2,2-dimethyl-1,3-dioxolan-4-ylmethylsulfonyl)phenyl]-1H-pyrrole-2,5-dione. MS (ESI): (M$^{+H)+}$ 481.

Example 21

Synthesis of 3-(1-methylindol-3-yl)-4-[3-((R)-2,3-dihydroxypropylsulfanyl)phenyl]-1H-pyrrole-2,5-dione

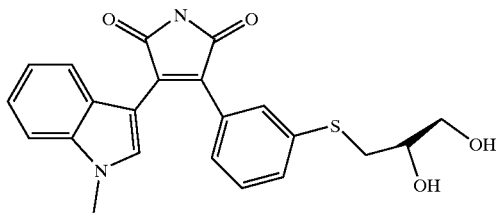

Toluenesulfonic acid (10 mg) was added to a solution of 3-(1-methylindol-3-yl)-4-{3-((R)-2,2-dimethyl-1,3-dioxolan-4-ylmethylsulfanyl)phenyl]-1H-pyrrole-2,5-dione (60 mg) in methanol (10 mL) and water (1 mL) and the reaction mixture was heated at 50° C. for 2 h. The volatiles were removed and the residue was partitioned between water and EtOAc. The organic layer was washed with NaCl (sat.) and dried over sodium sulfate. The crude product was purified on a silica gel column with 10/45/45 of MeOH/CH$_2$Cl$_2$/hexane and further purified by recrystallization from CH$_2$Cl/hexane to give 3-(1-methylindol-3-yl)-4-[3-((R)-2,3-dihydroxypropylsulfanyl)phenyl]-1H-pyrrole-2,5-dione (47 mg). MS (EI): M$^+$ 408.

Following the procedure described above but substituting 3-(1-methylindol-3-yl)-4-{3-((R)-2,2-dimethyl-1,3-dioxolan-4-ylmethylsulfanyl)phenyl]-1H-pyrrole-2,5-dione with 3-(1-methylindol-3-yl)-4-{3-((R)-2,2-dimethyl-1,3-dioxolan-4-ylmethylsulfinyl)phenyl]-1H-pyrrole-2,5-dione gave 3-(1-methylindol-3-yl)4-[3-((R)-2,3-dihydroxypropylsulfinyl)-phenyl]-1H-pyrrole-2,5-dione. MS (ESI): (M+H)$^+$ 425.

Following the procedure described above but substituting 3-(1-methylindol-3-yl)-4-{3-((R)-2,2-dimethyl-1,3-dioxolan-4-ylmethylsulfanyl)phenyl]-1H-pyrrole-2,5-dione with 3-(1-methylindol-3-yl)-4-{3-((R)-2,2-dimethyl-1,3-dioxolan-4-ylmethylsulfonyl)phenyl]-1H-pyrrole-2,5-dione gave 3-(1-methylindol-3-yl)-4-[3-((R)-2,3-dihydroxypropylsulfonyl)-phenyl]-1H-pyrrole-2,5-dione. MS (ESI): (M+H)$^+$ 441.

Example 22

Synthesis of 3-{3-[(2,3-dihydroxypropyl)amino]phenyl}-4-[5-fluoro-1-(3-hydroxypropyl)-1H-indol-3-yl]-1H-pyrrole-2,5-dione

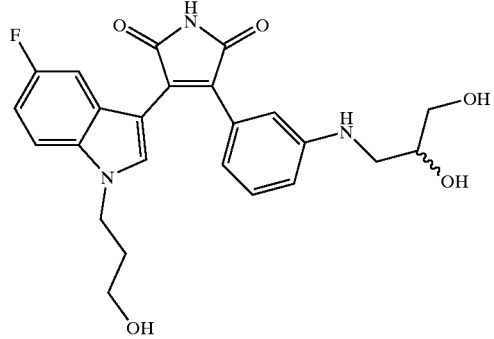

Step 1

Chlorotriphenylmethane (14.64 g, 52.5 mmol) was added at once to a solution of 3-bromo-1-propanol (6.95 g, 62.5 mmol) in pyridine (30 mL) under argon. The solution was stirred under argon for 12 hours and a precipitate formed. It was filtered and washed with pyridine. The filtrate was stripped and combined with the previous precipitate. This substance was purified via column chromatography (SiO$_2$, 5% CH$_2$Cl$_2$/Hexane then 10% CH$_2$Cl$_2$/Hexane). The colorless oil (5.2 g) was allowed to solidify and was recrystallized from hexane to provide the protected alcohol (5.2 g).

Step 2

To a solution of sodium hydride (60%, 0.44 g, 10.9 mmol) in dimethylformamide (8 mL) under argon at room temperature was added 5-fluoroindole (0.98 g, 7.25 mmol) in dimethylformamide (10 mL). The resultant solution was stirred for 1 hour and then cooled to 0° C. The bromide (Step 1—above, 4.15 g, 10.9 mmol) in dimethylformamide (15 mL) was added and the reaction was allowed to come to room temperature and stir for 12 hours. The mixture was poured in water (200 mL) and extracted with ethyl acetate (2×). The organic solution was washed with water (2×) and dried (brine, MgSO$_4$). Evaporation under reduced pressure provided a colorless oil (4.9 g) which was purified through chromatography (SiO$_2$, 5% ETOAc-Hexane) yielding the indole as a white solid (2.98 g).

Step 3

The alkylated fluoroindole (Step 2—above) was converted to the nitroaryl indole through procedures previously described in Example 7, steps 1–3.

Step 4

A suspension of nitroaryl indole (Step 3—above, 0.7 g, 10.7 mmol), triirondodecacarbonyl (0.65 g, 1.3 mmol), and absolute ethanol (30 mL) was refluxed overnight under argon. The hot mixture was filtered through a Buchner funnel packed tightly with celite and washed several times with hot methanol and hot 50% MeOH/EtOAc until most of the orange color was removed. Evaporation of the volatiles under reduced pressure and purification via chromatography (SiO$_2$, CH$_2$Cl$_2$, then 1% MeOH/CH$_2$Cl$_2$, then 2% MeOH/CH$_2$Cl$_2$) yielded the aniline as an orange solid (0.43).

Step 5

DL-glyceraldehyde(0.25 g, 1.38 mmol) in water (30 mL) was added to a solution of the aniline (Step 4—above, 0.43 g, 0.69 mmol) in MeOH (completely dissolved) under argon. The reaction was stirred for 30 minutes, sodium cyanoborohydride (89 mg, 1.38 mmol) was added and the mixture was stirred for 12 hours. Evaporation under reduced pressure and purification through chromatography (SiO$_2$, 5% MeOH/CH$_2$Cl$_2$/0.5% NH$_4$OH) provided the diol as an orange foam (295 mg).

Step 6

To a room temperature solution of the diol (Step 5—above, 0.245 g, 0.35 mmol) in methylene chloride (10 mL) under argon was added trifluoroacetic acid (0.16 mL, 2.22 mmol) followed by trifluoroacetic anhydride (0.3 mL, 2.11 mmol). The reaction was stirred for 10 minutes, cooled to 0° C. and triethylamine (0.6 mL) was added. The solution was stirred for 15 minutes, water (0.5 ml) was added and the reaction was poured into MeOH (10 mL). Evaporation of the volatiles under reduced pressure yielded a crude reaction residue. This was dissolved in methylene chloride, washed with brine (5%) and evaporated in vacuo. The resultant material was dissolved in methylene chloride/methanol (50%) and treated with triethylamine. (1–2 mLs) and evaporated under reduced pressure. Purification via chromatography (SiO$_2$, CH$_2$Cl$_2$ then 5% MeOH/CH$_2$Cl$_2$) provided the free base. Addition of hydrochloric acid in ether (1M, 2 eq.) followed by removal of the volatiles yielded 3-{3-[(2,3-dihydroxypropyl)amino]phenyl}-4-[5-fluoro-1-(3-hydroxypropyl)-1H-indol-3-yl]-1H-pyrrole-2,5-dione (94 mg). MP 118–125°: MS(EI): (M+H)$^+$ 454.

Example 23

Synthesis of 3-(5-fluoro-1-methyl-1H-indol-3-yl)-4-[3-(4-hydroxypiperidin-1-yl)phenyl]-1H-pyrrole-2,5-dione

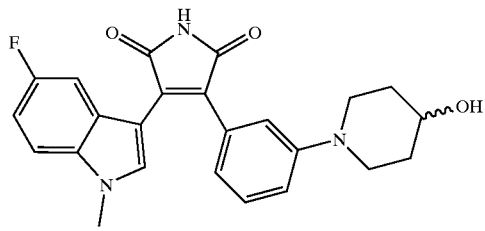

Step 1

To a room temperature solution of 3-bromophenethyl alcohol alcohol (1.22 g, 6.05 mmoles) in methylene chloride (20 mL) and dihydrofuran (2.54 g, 30.3 mmoles) was added p-toluenesulfonic acid monohydrate (11.5 mg, 0.06 mmoles). The reaction was stirred for 30 minutes followed by the addition of ether (50 mL). The organic solution was washed with saturated aqueous sodium bicarbonate solution (50 mL), dried (MgSO$_4$), and evaporated under reduced pressure to an oil (3.5 g). This was purified via flash chromatography (SiO$_2$, 4% EtOAc/Hexane) providing 2-[2-(3-bromophenyl)ethoxy]tetrahydro-2H-pyran, as a colorless liquid (1.4 g).

Step 2

The tetrahydropyran (Step 1—above, 0.40 g, 1.97 mmoles), BINAP (90 mg, 0.295 mmoles), Pd$_2$(dba)$_3$ (90 mg, 0.0486 mmoles), anhydrous sodium t-butoxide (0.28 g) were suspended in toluene (20 mL) under argon. 4-{[tert-butyl(diphenyl)silyl]oxy}piperidine (0.67 g, 1.97 mmoles) was then added and the reaction was stirred at 100° for 12 hours. After cooling to room temperature, ether (50 mL) was added, the reaction mixture was filtered through celite and washed with additional ether (25 mL). Evaporation under reduced pressure and purification through chromatography (SiO$_2$, 5% to 7% EtOAc/Hexane) yielded 4-{[tert-butyl(diphenyl)silyl]oxy}-1-{3-[2-(tetrahydro-2H-pyran-2-yloxy)ethyl]phenyl}piperidine as a tan oil (0.674 g, 1.24 mmoles).

Step 3

A solution of the piperidine (Step 2—above, 0.64 g, 1.18 mmoles) in acetic acid/tetrahydrofuran/water (4:2:1) was stirred under argon at 50° for 24 hours. After removal of the volatiles via evaporation, toluene was added and the reaction was evaporated a second time. Purification via flash chromatography (SiO$_2$, 10% EtOAc/Hexane) yielded the primary alcohol (0.42 g, 0.914 mmoles).

Step 4

To a 0° solution of the alcohol (Step 3—above, 0.42 g, 0.914 mmoles) in acetone (6 mL) was added Jones Reagent (1.9 M, 1.05 mL) dropwise. The solution was stirred at 0° C. for 1 hour, warmed to room temperature and allowed to stir for an additional 2 hours. Isopropanol (10 mL) was added dropwise, the reaction was filtered through celite and washed with acetone (40 mL). The filtrate was evaporated under reduced pressure, water was added and the mixture was extracted with ethyl acetate (2×). The organic solution was dried (brine, MgSO$_4$), and evaporated in vacuo to provide the carboxylic acid as a solid (100 mg, 0.21 mmoles).

Step 5

To a room temperature solution of the acid (Step 4—above, 100 mg, 0.21 mmoles) in methylene chloride (5 mL) under argon was added oxalyl chloride (22 µL) dropwise. The reaction was stirred for 2 hours, cooled to 0° and ammonia hydroxide (0.5 mL) was added dropwise. The mixture was stirred at room temperature for 1 hour and evaporated under reduced pressure. The crude mixture was dissolved in methylene chloride, filtered and evaporated in vacuo to yield the amide (94.5 mg, 0.2 mmoles).

Step 6

To a 0° C. solution of 1-methylindole (7.58 g, 50 mmoles) in dry ether (75 mL) under argon was added oxalyl chloride (4.36 mL, 50 mmoles) slowly. The resulting suspension was stirred for 30 minutes. After cooling to −65° C, sodium methoxide (22.9 mL, 100 mmoles, 25% in MeOH) was added dropwise at a rate to maintain −60° C. After the addition was complete, the reaction was allowed to warm to room temperature and stir for 2 hours. Water was added (30 mL) and the crude mixture was stirred then filtered. The resultant solid was washed with water, ether and then air dried. Purification of the crude product via flash chromatography (SiO$_2$, 20% to 40% ethyl acetate/Hexane—gradient) provided methyl (1-methyl-1H-indol-3-yl)(oxo)acetate as a solid (9 g, 41.4 mmoles).

Step 7

To a 0° C. of methyl (1-methyl-1H-indol-3-yl)(oxo)acetate (Step 6-above, 51.3 mg, 0.237 mmoles) and 2-[3-(4-{[tert-butyl(diphenyl)silyl]oxy}piperidin-1-yl)phenyl]acetamide (Step 5—above, 93.3 mg, 0.197 mmoles) in tetrahydrofuran (10 mL) was added dropwise a solution of potassium t-butoxide (0.59 mL, 0.591 mmoles, 1M in THF). The reaction was stirred at room temperature for 12 hours. Water was added to the suspension and the mixture was extracted with ether (2×), dried (brine, MgSO$_4$). Evaporation of the volatiles under reduced pressure and purification via flash chromatography (SiO$_2$, 1% MeOH/CH$_2$Cl$_2$) provided the indole (54 mg, 0.084 mmoles).

Step 8

To a room temperature solution of the indole (Step 7—above, 52 mg, 0.0812 mmoles) in dry tetrahydrofuran (3 mL) under argon was added tetrabutlyammonium fluoride (0.122 mL, 0.122 mmoles, 1 M in THF). The reaction was stirred for 12 hours and then water (25 mL) was added. The mixture was extracted with ethyl acetate (2×), dried (brine, MgSO$_4$), and evaporated in vacuo. Purification of the resultant product via flash chromatography (SiO$_2$, 4% MeOH/CH$_2$Cl$_2$) provided 3-[3-(4-hydroxypiperidin-1-yl)phenyl]-4-(1-methyl-1H-indol-3-yl)-1H-pyrrole-2,5-dione as a powder (29.9 mg, 0.0745 mmoles). MP 136–141°: MS(EI): (M+H)$^+$ 402.

Example 24

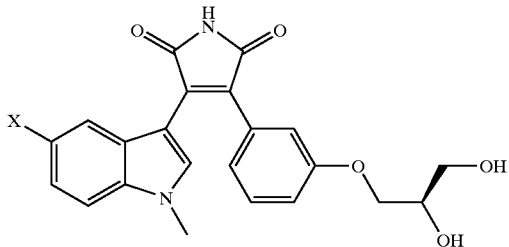

Following the procedure described in examples 1 and 2, but substituting N-methylindole with N-methyl-5-chloroindole and N-methyl-5-fluoroindole in step 4 of example 1 gave give 3-(1-methyl-5-chloroindol-3-yl)-4-{3-[((R)-2-hydroxy-2-hydroxymethyl)ethyloxy]phenyl}-1H-pyrrole-2,5-dione (MS (EI): (M+H)$^+$ 427); and 3-(1-methyl-5-fluoroindol-3-yl)-4-{3-[((R)-2-hydroxy-2-hydroxymethyl)ethyloxy]phenyl}-1H-pyrrole-2,5-dione (MS (EI): (M+H)$^+$ 411), respectively.

Example 25

Synthesis of 3-(5-methoxy-1-methylindol-3-yl)-4-{3-[(2,3-dihydroxy-propyl)amino]phenyl}-1H-pyrrole-2,5-dione

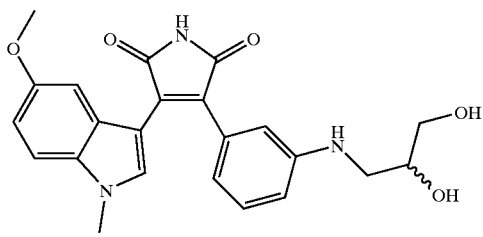

Step 1
A mixture of 5-methoxyindole-2-Carboxylic Acid (6 g, 31.4 mmol) and basic Copper(II) carbonate(0.6 g) was heated to 230° C.–240° C. under N$_2$ for five to six hours. After cooling, the resulting black gum was treated with benzene and filtered. The filtrate was concentrated and purified by flash column with 9/1 Hex/EtOAc then with 6/1 Hexane/EtOAc. The desired product, 5-methoxyindole (3.1 g) was obtained (61.6%). MS (EI): (M$^+$+1) 148.
Step 2
To a solution of 5-methoxyindole (1 g, 6.8 mmol) in 8 mL of DMF were added potassium hydroxide (0.92 g, 2.4 eq.) and methyl iodide (1 mL, 16 mmol). The resulting mixture was stirred at room temperature overnight. After removing volatile, the residue was diluted with EtOAc and washed with water (4×). The organic layer was dried and concentrated to afford 0.9 g (82%) 5-methoxy-1-methylindole. MS (EI): (M$^+$+1) 162.
Step 3
3-(5-methoxy-1-methylindol-3-yl)-4-(3-nitrophenyl)furan-2,5-dione was prepared by proceeding as described in Example 7, step 1 and 2, but substituting 5-methoxy-1-methylindole for 1-methylindole.

Step 4
3-(5-methoxy-1-methylindol-3-yl)-4-(3-nitrophenyl)-1H-pyrrole-2,5-dione was prepared by proceeding as described in Example 7, step 3, but substituting 3-(5-methoxy-1-methylindol-3-yl)-4-(3-nitrophenyl)furan-2,5-dione for 3-(1-methylindol-3-yl)-4-(3-nitrophenyl)furan-2,5-dione.
Step 5
3-(5-methoxy-1-methylindol-3-yl)-4-(3-aminophenyl)-1H-pyrrole-2,5-dione was prepared by proceeding as described in Example 7, step 4, but substituting 3-(5-methoxy-1-methylindol-3-yl)-4-(3-nitrophenyl)-1H-pyrrole-2,5-dione for 3-(1-methylindol-3-yl)-4-(3-nitrophenyl)-1H-pyrrole-2,5-dione.
Step 6
3-(5-methoxy-1-methyl-1H-indol-3-yl)-4-{3-[(2,3-dihydroxy-propyl)amino]phenyl}-1H-pyrrole-2,5-dione was prepared as described in Example 7, step 5, but substituting 3-(5-methoxy-1-methylindol-3-yl)-4-(3-aminophenyl)-1H-pyrrole-2,5-dione for 3-(1-methylindol-3-yl)-4-(3-aminophenyl)-1H-pyrrole-2,5-dione. MS (EI): M$^+$ 421

Following the procedure described above, but substituting 5-methylindole-2-carboxylic acid for 5-methoxylindole-2-carboxylic Acid in step 1 afforded 3-(1,5-dimethyl-1H-indol-3-yl)-4-{3-[(2,3-dihydroxy-propyl)amino]phenyl}-1H-pyrrole-2,5-dione. MS (EI): M$^+$ 405.

Example 26

Synthesis of 3-(5-isopropoxy-1-methylindol-3-yl)-4-{3-[(2,3-dihydroxy-propyl)amino]phenyl}-1H-pyrrole-2,5-dione

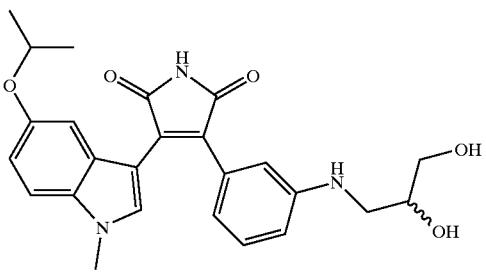

Step 1
A mixture of 3-methyl-4-nitrophenol (4.59 g, 0.03 mol) and 2-bromopropane (4.06 g, 0.033 mol) was refluxed with potassium carbonate (10 g) in acetone (200 mL) for 5 hours. After cooling, the reaction mixture was filtered through celite and the residue was purified by flash column (9/1 of Hexane/EtOAc) to afford 3.42 g of 4-isopropoxy-2-methyl-1-nitrobenzene (58.5%).
Step 2
A mixture of 4-isopropoxy-2-methyl-1-nitrobenzene (3.55 g,0.018 mol) and tert-butoxybis(dimethylamino)methane (9 mL) was refluxed for 4 hours and the volatile was removed. The dark brown residue was dissolved in THF (150 mL) and hydrogenated with catalytic amount of 10% Pd on Carbon with H$_2$ in a balloon. After stirring at room temperature overnight, the catalyst was filtered off and the filtrate was concentrated to afford 3.07 g 5-isopropoxyindole (96%). MS(EI): (M$^+$1) 176.

Step 3

Procedure described in Example 24, step 2 through step 6 was followed, but substituting 5-isopropoxyindole for 5-methoxyindole to provide 3-(5-isopropoxy-1-methyl-indol-3-yl)-4-{3-[(2,3-dihydroxy-propyl)amino]phenyl}-1H-pyrrole-2,5-dione. MS (EI): M+ 449.

Example 27

Synthesis of 3-(1-methyl-indol-3-yl)-4-{3-((R)-2,3-dihydroxy-propoxyl)-2-methylphenyl}-1H-pyrrole-2,5-dione

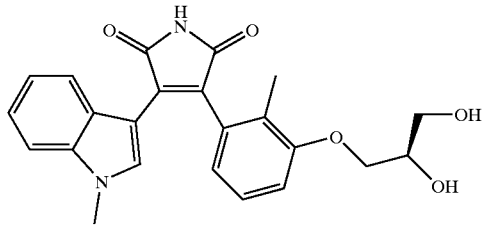

Step 1

To a methanol solution (25 mL) at 0° C. was dropwise added thionyl chloride (9.6 mL, 0.13 mol). After 15 minutes, 3-hydroxy-2-methylbenzoic acid (4 g, 0.033 mol) was added and the resulting mixture was stirred at room temperature for 24 hours. Volatile was removed under vacuo and the residue was partitioned between water and ethyl acetate. The organic layer was separated, washed with water and saturated sodium chloride solution, and was dried over sodium sulfate. After concentration, the crude product was recrystallized from dichloromethane and hexane to gave 3.48 g of methyl 3-hydroxy-2-methylbenzoate.

Step 2

To a solution of methyl 3-hydroxy-2-methylbenzoate (3.0 g, 18 mmol) in N-methylpyrrolidinone (30 mL) was added (R)-2,2-dimethyl-1,3-dioxolan-4-ylmethyl p-tosylate (6.2 g, 1.2 eq.), and followed by $K_2CO_3$ (7.5 g, 3 eq.). After the mixture was heated at 96° C. overnight, it was cooled to room temperature, quenched with $H_2O$, and partitioned between $H_2O$ and EtOAc. The organic layer was separated, washed with $H_2O$ and NaCl (sat.), and then dried over $Na_2SO_4$. The crude product was purified on a silica gel column with 20% EtOAc in hexane to give methyl 3-((R)-2,2-dimethyl-1,3-dioxolan-4-ylmethyloxy)-2-methylbenzoate as an oil (4.5 g).

Step 3

Methyl 3-((R)-2,2-dimethyl-1,3-dioxolan-4-ylmethyloxy)-2-methylbenzoate (4.2 g, 15 mmol) was dissolved in 20 mL of methanol and 1 mL of water. To the above solution was added lithium hydroxide (2.4 g, 5eq.). After stirring the reaction mixture at room temperature for 4 h, the volatile was removed under vacuo and the residue was partitioned between EtOAc and $H_2O$. The aqueous layer was separated, cooled with an ice bath, and then acidified with 10% aq. HCl. The acidic aqueous layer was extracted with EtOAc. The EtOAc layer was washed with NaCl (sat.), dried over $Na_2SO_4$, and concentrated to give 3-((R)-2,2-dimethyl-1,3-dioxolan-4-ylmethyloxy)benzoic acid as a white solid (4 g).

Step 4

To a solution of 3-((R)-2,2-dimethyl-1,3-dioxolan-4-ylmethyloxy)-2-methylbenzoic acid (2.4 g, 9 mmol) in 20 mL of dichloromethane was added oxalyl chloride (0.86 mL, 1.1 eq.). The resulting mixture was stirred at room temperature in the presence of a catalytic amount of DMF. Bubbles formed and stirring continued until no more bubbles were generated. Volatile was removed under vacuo and the residue was suspended in ether (20 mL) and was added dropwise to an ether solution (60 mL) at 0° C. containing diazomethane generated from N-nitroso-N-methylurea (6.95 g, 7.5 eg.) and 19 g of potassium hydroxide according to the procedure described by Berkowitz, D. B. in J. Org. Chem. 65, 847, (2000). The resulting mixture was stirred at 0° C. for 1 h and was allowed to warm to room temperature, where it was stirred for another hour. Excess amount of diazomethane was quenched with acetic acid and the volatile was removed under vacuo. The residue was purified on a silica gel column with 10% ethyl acetate in hexane to give 0.8 g of 2-diazo-1-[3-((R)-2,2-dimethyl-[1,3]-dioxolan-4-ylmethoxy)-2-methyl-phenyl]ethanone.

Step 5

To a solution of 2-diazo-1-[3-(2,2-dimethyl-[1,3]-dioxolan-4-ylmethoxy)-2-methylphenyl]ethanone (0.5 g, 1.73 mmol) in 20 mL of methanol at room temperature was added dropwise a solution of silver benzoate (52 mg, 13%) in 2.6 mL of triethylamine. The solution turned greenish and then brown, black precipitate formed. After stirring for 1.5 h, it was filtered through celite and the filtrate was concentrated. The residue was then purified on a silica gel column with 20% ethyl acetate in hexane to afford 0.43 g of [3-((R)-2,2-dimethyl-[1,3]dioxolan-4-ylmethoxy)-2-methylphenyl] acetic acid methyl ester. The above ester was then hydrolyzed by stirring with lithium hydroxide (0.25 g) in 5 mL of methanol at room temperature to give 0.4 g of [3-((R)-2,2-dimethyl-[1,3]dioxolan-4-ylmethoxy)-2-methylphenyl] acetic acid.

Step 6

3-(1-methylindol-3-yl)-4-[3-(R)-2,2-dimethyl-[1,3]dioxolan-4-ylmethoxy)-2-methylphenyl]furan-2,5-dione was prepared according to the procedure described in Example 1, step 4, but substituting [3-((R)-2,2-dimethyl-[1,3]dioxolan-4-ylmethoxy)-2-methylphenyl] acetic acid for 3-((R)-2,2-dimethyl-[1,3]dioxolan-4-ylmethoxy) phenylacetic acid.

Step 7

3-(1-methylindol-3-yl)-4-[3-(R)-2,2-dimethyl-[1,3]dioxolan-4-ylmethoxy)-2-methylphenyl]-1H-pyrrole-2,5-dione was prepared according to the procedure described in Example 1, step 5, but substituting 3-(1-methylindol-3-yl)-4-[3-((R)-2,2-dimethyl-[1,3]dioxolan-4-ylmethoxy))-2-methylphenyl]furan-2,5-dione for 3-(1-methylindol-3-yl)-4-[3-((R)-2,2-dimethyl-[1,3]dioxolan-4-ylmethoxy)phenyl]furan-2,5-dione.

Step 8

3-(1-methylindol-3-yl)-4-[3-((R)-2,3-dihydroxypropoxy)-2-methylphenyl]-1H-pyrrole-2,5-dione was according to the procedure described in Example 2, step 1, but substituting 3-(1-methylindol-3-yl)-4-[3-((R)-2,2-dimethyl-[1,3]dioxolan-4-ylmethoxy)-2-methylphenyl]-1H-pyrrole-2,5-dione for 3-(1-methylindol-3-yl)-4-[3-((R)-2,2-dimethyl-[1,3]dioxolan-4-ylmethoxy)phenyl]-1H-pyrrole-2,5-dione. MS (EI): (M++1) 407.

Example 28

Synthesis of 3-(1-methyl-indol-3-yl)-4-{3-((R)-2,3-dihydroxy-propoxyl)-2-nitrophenyl}-1H-pyrrole-2,5-dione

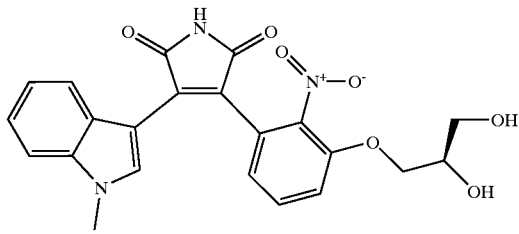

Step 1

To a methanol solution (15 mL) at 0° C. was dropwise added thionyl chloride (6.4 mL, 0.088 mol). After 15 minutes, 3-hydroxy-2-nitrobenzoic acid (4 g, 0.022 mol) was added and the resulting mixture was stirred at room temperature for 72 hours. Volatile was removed under vacuo and the residue was partitioned between water and ethyl acetate. The organic layer was separated, washed with water and saturated sodium chloride, and was dried over sodium sulfate. After concentration, the crude product was recrystallized from dichloromethane and hexane to gave 4.5 g of methyl 3-hydroxy-2-nitrobenzoate.

Step 2

To a solution of methyl 3-hydroxy-2-nitrobenzoate (1.97 g, 10 mmol) in N-methylpyrrolidinone (15 mL) was added (R)-2,2-dimethyl-1,3-dioxolan-4-ylmethyl p-tosylate (3.43 g, 1.2 eq.), and followed by $K_2CO_3$ (4.2 g, 3 eq.). After the mixture was heated at 96° C. overnight, it was cooled to room temperature, quenched with $H_2O$, and partitioned between $H_2O$ and EtOAc. The organic layer was separated, washed with $H_2O$ and NaCl (sat.), and then dried over $Na_2SO_4$. The crude product was purified on a silica gel column with 20% EtOAc in hexane to give methyl 3-((R)-2,2-dimethyl-1,3-dioxolan-4-ylmethyloxy)-2-nitrobenzoate as an oil (3.1 g).

Step 3

Methyl 3-((R)-2,2-dimethyl-1,3-dioxolan-4-ylmethyloxy)-2-nitrobenzoate (2.8 g, 9 mmol) was dissolved in 25 mL of methanol and 2 mL of water. To the above solution was added lithium hydroxide (1.13 g, 3 eq.). After stirring the reaction mixture at room temperature for 5 h, the volatile was removed under vacuo and the residue was partitioned between EtOAc and $H_2O$. The aqueous layer was separated, cooled with an ice bath, and then acidified with 10% aq. HCl. The acidic aqueous layer was extracted with EtOAc. The EtOAc layer was washed with NaCl (sat.), dried over $Na_2SO_4$, and concentrated to give 3-((R)-2,2-dimethyl-1,3-dioxolan-4-ylmethyloxy)-2-nitrobenzoic acid as a white solid (1.9 g).

Step 4

To a solution of 3-((R)-2,2-dimethyl-1,3-dioxolan-4-ylmethyloxy)-2-nitrobenzoic acid (1.9 g, 6.4 mmol) in 20 mL of dichloromethane was added oxalyl chloride (0.55 mL, 1.1 eq.). The resulting suspension was stirred at room temperature in the presence of catalytic amount of DMF. Bubbles formed, and stirring continued until no more bubbles were generated while the suspension turned into a solution. Volatile was removed under vacuo and the residue was suspended in ether (15 mL) and was added dropwise to an ether solution (40 mL) at 0° C. containing diazomethane generated from N-nitroso-N-methylurea (4.95 g, 7.5 eg.) and 13.5 g of potassium hydroxide according to the procedure described by Berkowitz, D. B. in J. Org. Chem. 65, 847, (2000). The resulting mixture was stirred at 0° C. for 1 h and was allowed to warm to room temperature, where it was stirred overnight. Excess of diazomethane was quenched with acetic acid and the volatile was removed under vacuo. The residue was purified on a silica gel column with 2/4/4 of acetone/dichloromethane/hexane to give 0.95 g of 2-diazo-1-[3-((R)-2,2-dimethyl-[1,3]-dioxolan-4-ylmethoxy)-2-nitrophenyl]ethanone.

Step 5

To a solution of 2-diazo-1-[3-(2,2-dimethyl-[1,3]-dioxolan-4-ylmethoxy)-2-nitrophenyl]ethanone (0.9 g, 2.8 mmol) in 30 mL of methanol at room temperature was added dropwise a solution of silver benzoate (84 mg, 13%) in 4.2 mL of triethylamine. The solution turned greenish and then brown, black precipitate formed. After stirring for 1.5 h, it was filtered through celite and the filtrate was concentrated. The residue was then purified on a silica gel column with 20% ethyl acetate in hexane to afford 0.75 g of [3-((R)-2,2-dimethyl-[1,3]dioxolan-4-ylmethoxy)-2-nitrophenyl] acetic acid methyl ester. The above ester (0.52 g, 1.6 mmol) was then hydrolyzed by stirring with lithium hydroxide (0.27 g) in 5 mL of methanol at room temperature to give 0.5 g of [3-((R)-2,2-dimethyl-[1,3]dioxolan-4-ylmethoxy)-2-nitrophenyl] acetic acid.

Step 6

3-(1-methylindol-3-yl)-4-[3-(R)-2,2-dimethyl-[1,3]dioxolan-4-ylmethoxy)-2-nitrophenyl]furan-2,5-dione was prepared according to the procedure described in Example 1, step 4, but substituting [3-((R)-2,2-dimethyl-[1,3]dioxolan-4-ylmethoxy)-2-nitrophenyl] acetic acid for 3-((R)-2,2-dimethyl-[1,3]dioxolan-4-ylmethoxy) phenylacetic acid.

Step 7

3-(1-methylindol-3-yl)-4-[3-(R)-2,2-dimethyl-[1,3]dioxolan-4-ylmethoxy)-2-nitrophenyl]-1H-pyrrole-2,5-dione was prepared according to the procedure described in Example 1, step 5, but substituting 3-(1-methylindol-3-yl)-4-[3-((R)-2,2-dimethyl-[1,3]dioxolan-4-ylmethoxy))-2-nitrophenyl]furan-2,5-dione for 3-(1-methylindol-3-yl)-4-[3-((R)-2,2-dimethyl-[1,3]dioxolan4-ylmethoxy)phenyl]furan-2,5-dione.

Step 8

3-(1-methylindol-3-yl)-4-[3-((R)-2,3-dihydroxypropoxy)-2-nitrophenyl]-1H-pyrrole-2,5-dione was according to the procedure described in Example 2, step 1, but substituting 3-(1-methylindol-3-yl)-4-[3-((R)-2,2-dimethyl-[1,3]dioxolan-4-ylmethoxy)-2-nitrophenyl]-1H-pyrrole-2,5-dione for 3-(1-methylindol-3-yl)-4-[3-((R)-2,2-dimethyl-[1,3]dioxolan-4-ylmethoxy)phenyl]-1H-pyrrole-2,5-dione. MS (EI): ($M^+$+1) 438.

Following the procedure described above, but substituting 5-hydroxy-2-nitrobenzoic acid for 3-hydroxy-2-nitrobenzoic acid gave 3-(1-methylindol-3-yl)-4-{5-((R)-2,3-dihydroxy-propoxyl)-2-nitrophenyl}-1H-pyrrole-2,5-dione. MS (EI): ($M^+$+1) 438.

Formulation Examples

The following are representative pharmaceutical formulations containing a compound of Formula (I).

Example 1

Tablet formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2

Capsule formulation

The following ingredients are mixed intimately and loaded into a hard-shell gelatin capsule.

| Quantity per Ingredient | capsule, mg |
|---|---|
| compound of this invention | 200 |
| lactose, spray-dried | 148 |
| magnesium stearate | 2 |

Example 3

Suspension formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Example 4

Injectable formulation

The following ingredients are mixed to form an injectable formulation.

| Ingredient | Amount |
|---|---|
| compound of this invention | 0.2 mg–20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Biological Examples

Example 1

Inhibition of Glycogen Synthase Kinase-3β—in vitro assay

The in vitro GSK-3β inhibitory activity of compounds of this invention was determined with a truncated form of recombinant rabbit GSK-3β enzyme.

Isolation of GSK-3β

The construct was cloned in pGEX-3X vector according to the procedure described in Wang, Q. M. et al., *J. Biol. Chem.* 269, 14566–14574 (1994). Ten amino acids at the N-terminus were deleted to obtain constitutively active GSK-3β ((see Murai H. et al., *FEBS Lett.* 392,153–60, (1996)). GSK-3β was expressed in BL21 DE3 cells. The cells were grown at 37° C. until they reached mid log phase and then induced with isopropyl-beta-(D)-thiogalactopyranoside (final concentration 0.4 mM) at 30° C. for 2 h. The cells were homogenized and the cell extract was loaded on a glutathione sepharose 4B column. GSK-3β was eluted with glutathione buffer (50 mM Tris pH 8 and 10 mM reduced glutathione). The eluate was collected in 3 minute fractions and assayed for GSK-3β content on a 10% SDS PAGE (polyacrylamide gel electrophoresis). Fractions above 20% peak height were pooled, aliquoted, and stored at –80° C. until used.

Inhibition of GSK-3β

The GSK-3β binding assay was performed in 50 μl reactions in a 96 well polypropylene plate, each reaction containing 20 mM magnesium chloride, 40 μM ATP, 2 mM DTT, 88.5 μM biotinylated and phosphorylated CREB-peptide substrate (biotin-KRREILSRRPS($PO_4$)YR-OH, see Wang, Q. M. et al., *J. Biol. Chem.* 269, 14566–14574 (1994)), [γ-$^{33}$P] ATP (1 μCi), and 2 μl of compounds of this invention in DMSO (various concentrations). 15 μl of GSK-3β (various concentrations) was added and the reaction mixture was incubated at 30° C. for 1 h. The reaction was stopped by transferring 25 μl of the reaction mixture to a phosphocellulose plate containing 130 μl of 1.85% phosphoric acid. The free radionucleotides in the membrane were washed off under vacuum with 1.85% phosphoric acid (5 times). After the last wash, the plate was transferred to an adoptor plate and 50 μl of scintillation cocktail (Microscint-20, Packard, cat. #20-133) was added to each well and the amount of radioactivity was counted in a top counter.

Compounds of this invention were active in this assay.

The GSK-3β inhibitory activities (expressed as $IC_{50}$, the inhibitor concentration causing 50% inhibition of the activity in the control) of some compounds of the invention disclosed in Table I–IV were less than 2 μm. Activities of certain specific compounds are shown below

| Compound | IC$_{50}$ μM |
|---|---|
| I-1 | 0.194 |
| II-1 | 0.02 |
| II-2 | 0.0264 |
| II-4 | 0.0296 |
| III-3 | 0.23 |
| IV-1 | 0.1334 |

Example 2

Inhibition of β-catenin degradation—in vitro assay

The cell based GSK-3β activity of compounds of this invention was determined by measuring β-catenin levels in Jurkat T-cells after treatment with the compounds of this invention using ELISA as follows.

Jurkat cells (5×105 cells/mL) were plated in 6-well plates (6 mL/well) and then treated with various concentrations of the compounds of this invention (preferrably 1 nM-10 μM) for 24 h. At the end of the incubation, the cells were collected and washed once with PBS. The cells were then suspended in 0.3 mL Radiolmmuno Precipitation Assay lysis (RIPA) buffer (Boehringer Mannheim, cat.#1 920 693). After 3 freeze—thaw cycles, the cell extracts were centrifuged at 15,000 rpm for 10 min. The supernatant was collected and analyzed using ELISA assay as described below.

96 Microwell plates were coated overnight with capture antibody (mouse monoclonal anti-β-catenin, Zymed La., cat.#13-8400, 100 μl per well, containing 250 ng antibody) diluted in coating buffer (0.1 M NaHCO$_3$, pH 9.5). The wells were aspirated and washed 3 times with 300 μl of wash buffer (PBS containing 0.05% Tween 20) and blocked with 200 μl of assay diluent (PBS, 10% RBS, pH 7; PharMingen) and then incubated at room temperature for at least 72 h. The wells were washed again as described above. 100 μl of the Jurkat cell supernatant and various concentrations of a catenin standard (Behrens et al. Nature, Vol. 382, p638 (1996)) were added to the wells and incubated for 2 h at room temperature. After incubation, the wells were washed and 100 μl of anti-β-catenin antibody (Santa Cruz, β-catenin H-102, sc-7199, rabbit IgG) diluted in assay diluent (1:1250) was added to each well and the cells were incubated at room temperature for 2 h. After washing, 100 μl of working detector (Sigma B5283, mouse monoclonal anti-rabbit IgG-Biotin) diluted in assay diluent (1:2000) was added into each well and incubated for 1 h at room temperature. 3,3',5,5'-Tetramethylbenzidine (PharMingen, Cat. #2642KK) was used for color development. The reaction was stopped by adding 50 μl of stop solution (2N H$_2$SO$_4$) to each well. The plates were read with an ELISA plate reader at 570 nm within 30 min., of stopping the reaction.

The level of GSK-3β inhibition was calculated by plotting the compound concentration versus β-catenin levels. The results are shown in FIG. 1, confirming the effect of compounds of this invention on β-catenin levels.

Example 3

Cytokine Secretion Assays—human T-cell assay

The effect of compounds of this invention on cytokine secretion levels from human CD4+ T-helper cells was determined as in Rogge et. al., J. Exp. Med. 185, 825–831 (1997).

For this assay, human neonatal leukocytes were isolated from freshly collected, heparinized neonatal blood by Ficoll-Paque (Pharmacia Biotech, Uppsala, Sweden) density gradient centrifugation. To generate Th1 and Th2 cell lines, CD8+ T cells were removed by positive selection with anti-CD8 microbeads and magnetic activated cell sorting according to a protocol supplied by the manufacturer (Miltenyi Biotec, Bergisch Gladbach, Germany). On day 0, cells were pre-incubated with various concentrations of test compound for one day. The next day, cells were stimulated with 2 μg/mL phytohemagglutinin (Wellcome, Beckenham, U.K.) in the presence of 2.5 ng/mL IL-12 (Hoffmann-La Roche, Nutley, N.J.) and 200 ng/mL neutralizing anti-IL-4 antibody (no.1 8500D; PharMingen, San Diego, Calif.) for Th1 cultures or 1 ng/mL IL-4 (PharMingen) and 2 μg/mL neutralizing anti-IL-12 antibody 17F7 and 20C2 (kindly provided by M. Gately, Hoffmann-LaRoche) for Th2 cultures, respectively. The cells were washed on day 3 and expanded in complete RPMI 1640 medium (Life Technologies, Milan, Italy), supplemented with compounds of this invention, 5% FetalClone I (HyClone, Logan, Utah), 2 mM L-glutamine, 1 mM sodium pyruvate, 100 U/mL penicillin-streptomycin, and containing 100 U/mL IL-2 (Hoffmann-La Roche). The cells were washed again on day 14 and 10$^5$ cells were re-stimulated in 96-well round-bottom plates for 24 h with plate-bound anti-CD3 and anti-CD28 monoclonal antibodies (clone TR[66]; see Lanzavecchia, A., and D. Scheidegger., Eur. J. Immunol. 17:105–111 (1987)) to measure IFN-gamma, IL-4, and IL-13 in culture supernatants by ELISA assays (Gallati, H., I. et al., J. Biol. Regul. Homeostatic Agents. 1:109–118, (1987)). The ED$_{50}$ values (concentration of compound that inhibits cytokine secretion to 50% of the maximal value) were determined by fitting a sigmoidal curve to the plotted data.

Compounds of this invention were active in this assay and showed suppression of IL-4, and IL-13 secretion levels, while Interferon-gamma levels remained unchanged.

Example 4

Cytokine Secretion Assays—murine T-cell assay

CD4+, CD62Lhi cells (naive T-cells) are isolated from the spleens of Balb/C Do11.10 OA-TCR transgenic mice (Murphy K. M. et al., Science, 250, 1720 (1990)) by Ficoll density gradient and Miltenyi magnetic immunobead separations. These naive T-cells were grown in co-culture with irradiated Balb/C splenocytes (T:APC of 1:25) under neutral conditions (without the addition of differentiating cytokines). T-cells are stimulated with 300 nM ovalbumin peptide (NH2-KISQAVHAAHAEINEAG-COOH) in the presence of different inhibitor concentrations (test compound), including controls with solvent only. At day 3 the cells were split 1:3, with inhibitors were added back to the medium to maintain the original concentration. On day 6, the cells were counted, washed, re-plated at a 1:25 ratio with irradiated Balb/C splenocytes, and re-stimulated with 300 nM ovalbumin peptide. On day 8, the supernatants were harvested and levels of IFN-gamma, IL-4, IL-5, and IL-13 were quantitated by ELISA (R&D Systems). The ED$_{50}$ values (concentration of compound that inhibits cytokine secretion to 50% of the maximal value) were determined by fitting a sigmoidal curve to the plotted data.

Compounds of this invention were active in this assay and led to a reduction in Th2 cytokine levels.

Example 5

Inhibition of Eosinophil influx into the lungs of Ovalbumin sensitized brown Norway rats—in vivo assay The ability of the compounds of the invention to inhibit leukocyte infiltration into the lungs was determined by measuring the inhibition of eosinophil accumulation into the bronchioalveolar lavage (BAL) fluid of Ovalbumin (OA) sensitized brown Norway rats after antigen challenge by aerosol. Briefly, male brown-Norway rats were sensitized i.p. with 100 jig of OA in 0.2 mL alum on Day 0, Day 7, and Day 14. On Day 21, the rats were challenged with 1% OA for 45 min., and sacrificed 72 h later. Test compounds or only vehicle (control group) were administered from the day before the third immunization until the end of the study. At the time of sacrifice, rats were anesthetized (urethane, approx. 2 g/kg, i.p.) and the lungs were lavaged with 3×3 mL BAL. The BAL fluid was analyzed for total leukocyte number and differential leukocyte counts. The total leukocyte number in an aliquot of the cells (20 μl) was determined by Coulter Counter. For differential leukocyte counts, 50–200 μl of the samples were centrifuged in a Cytospin and the slide stained with Diff-Quik. The proportions of monocytes, eosinophils, neutrophils and lymphocytes were counted under light microscopy using standard morphological criteria and expressed as a percentage.

Compounds of this invention were active in this assay and led to a reduction in monocytes, eosinophils, neutrophils and lymphocytes infiltration into the lungs.

Example 6

Reduction of total Serum IgE and Ovalbumin specific IgE in Ovalbumin sensitized A/J mice—in vivo assay This protocol was designed to examine the effect of compounds on IgE levels in the serum of Ovalbumin (OA) sensitized A/J mice. The primary endpoint was IgE production during sensitization. Briefly, male A/J mice (20–25 g) were sensitized by intraperitoneal injection of OA/Alum (10 μg in 0.2 mL Al(OH)$_3$; 2%) on Day 0, and Day 7. On Day 14, the mice were anesthetized with urethane and blood was drawn by cardiac puncture. Test compounds or only vehicle (control group) were administered from the day before the second OA/Alum injection until the end of the study. Total serum IgE and OA-specific IgE were measured by ELISA (Pharmingen, cat#2655KI, biotinylated ovalbumin for OA specific IgE) and compared between compound and vehicle treated groups.

Compounds of this invention were active in this assay and led to a reduction in IgE levels into the lungs.

Example 7

Differential Expression of TCF7 in Th1 and Th2 cells

Figure 2A:
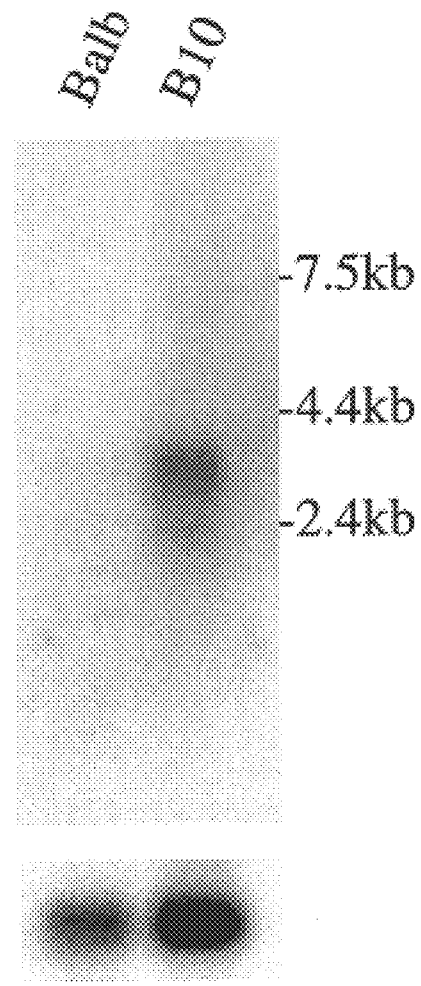
FIG. 2A shows expression of TCF7 transcripts in MRNA from the B10.D2 cells relative to that in Balb/C T-cells.
Figure 2B:
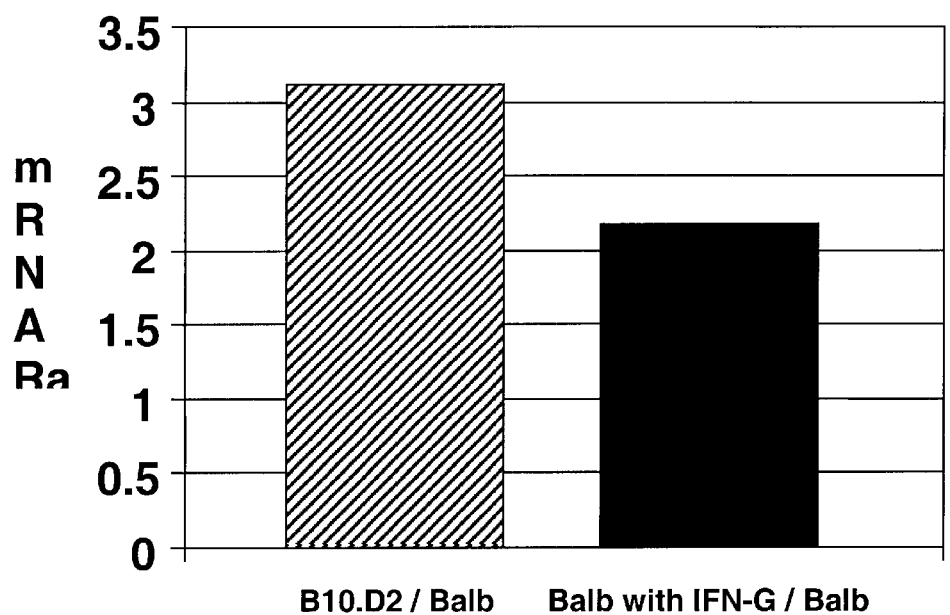
FIG. 2B shows the induction of TCF-7 by interferon-gamma.

CD4+, naive T-cells were prepared as described in Example 4 from Balb/C Do11.10 OA-TCR (+/+) transgenic mice and B10.D2 DO I1.10 OA-TCR(+/−) transgenic mice (Guler M. L. et al., J. Immunol. 162, 1339–1347, 1999). Cells were harvested at day 5 after initial stimulation with 300 nM ovalbumin peptide and mRNA was prepared (total RNA: Chomzynski and Sacchi, Anal. Biochem 162: 150–159, 1987, mRNA: Promega polyA tract) for expression analysis by Northern Blot. As hybridization probe clone AA119960 (Genbank) was labeled by random priming (GIBCO 18187-013) (FIG. 2A). As shown in FIG. 2A, expression of TCF7 transcripts was detected in mRNA from the B10.D2 preparation (Th-1 cells) while TCF7 transcripts were undetectable in the mRNA preparation from Balb/C T-cells (Th-2 cells). In a separate experiment, CD4+ naive T-cells from Balb/C Do11.10 OA-TCR (+/+) transgenic mice were either stimulated with 300 nM ovalbumin peptide and interferon-gamma or ovalbumin peptide for 5 days. mRNA was isolated and used in a quantitative RT-PCR (Baranzini et al., Journal of Immunology. 165: 6576–6582, 2000) to determine relative levels of TCF7-mRNA between ovalbumin induced samples from Balb/C and B10.D2 and relative levels of ovalbumin treated Balb/C samples vs. ovalbumin and IFN-G treated samples from Balb/C CD4+ T-cells. TCF7 primers for the quantitative RT-PCR were: AGCTGCAGCCATATGATAGAA and CTTGAGTGTG-CACTCAGCAA. Thus, as shown in FIG. 2B, interferon gamma, a cytokine that promotes Th1 differentiation of Balb/c T-cells, induces the expression of TCF7. Both these experiments confirm that TCF7 levels are linked to the T-helper response. High levels of TCF7 expression appeared to be linked to a Th1 response, while low levels are linked to a Th2 response.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound represented by Formula (I):

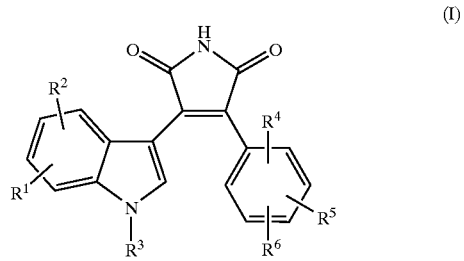

wherein:
  $R^1$ and $R^2$ independently represent hydrogen, alkyl, halo, haloalkyl, alkylthio, hydroxy, alkoxy, cyano, nitro, amino, acylamino, monoalkylamino, or dialkylamino;
  $R^3$ represents hydrogen, alkyl, cycloalkyl, heteroalkyl, —COR$^7$ (wherein R$^7$ is hydrogen or alkyl), or phenyl optionally substituted with one or two substituents independently selected from the group consisting of hydrogen, alkyl, haloalkyl, alkylthio, hydroxy, alkoxy, cyano, nitro, amino, acylamino, monoalkylamino, and dialkylamino;
  $R^4$ and $R^5$ independently represent hydrogen, alkyl, halo, haloalkyl, alkylthio, hydroxy, alkoxy, cyano, nitro, amino, acylamino, monoalkylamino, or dialkylamino;
  $R^6$ is heteroalkyl, heterocyclyl, heterocyclylalkyl, heteroalkylsubstituted heterocyclyl, heteroalkylsubstituted cycloalkyl, hetereosubstituted cycloalkyl, —OR$^8$, —S(O)$_n$R$^8$ (wherein n is 0 to 2; and R$^8$ is heteroalkyl, heteroaralkyl, heterocyclyl, or heterocyclylalkyl), —NR$^9$R$^{10}$ (wherein R$^9$ is hydrogen or alkyl and R$^{10}$ is heteroalkyl, heteroaralkyl, heterosubstituted cycloalkyl, heterocyclyl, or heterocyclylalkyl), or —X-(alkylene)—Y—Z (wherein X is a covalent bond, —O—, —NH—, or —S(O)$_{n1}$— where n1 is 0 to 2, and Y is —O—, —NH—, or —S—, and Z is heteroalkyl or SiR$^{11}$R$^{12}$R$^{13}$ where R$^{11}$, R$^{12}$ and R$^{13}$ are independently hydrogen or alkyl), or R$^6$ together with R$^4$ forms a methylenedioxy or ethylenedioxy group when they are adjacent to each other; or a pharmaceutically acceptable salt thereof.

2. The compound of claim 1 wherein R$^3$ is alkyl.

3. The compound of claim 2 wherein R$^3$ is methyl.

4. The compound of claim 1 wherein R$^6$ group is at the 3-position of the phenyl ring and is heteroalkyl, heterocyclylalkyl, —OR$^8$ (wherein R$^8$ is heteroalkyl or heterocyclylalkyl), —NHR$^{10}$ (wherein R$^{10}$ is heteroalkyl, heterosubstituted cycloalkyl, heterocyclyl, or heterocyclylalkyl), or —X— (alkylene)-Y-heteroalkyl (wherein X is a covalent bond, —O— or —NH— and Y is —O— or —NH).

5. The compound of claim 4 wherein R$^6$ is (RS), (R) or (S) 2-hydroxy-2-hydroxymethylethyloxy, 3-hydroxypropyloxy, 2-aminoethyloxy, 3-aminopropyloxy, 2-morpholin-4-ylethyloxy, or (RS), (R) or (S) 2,2-dimethyl-1,3-dioxolan-4-ylmethyloxy.

6. The compound of claim 4 wherein R is (RS), (R) or (S) 2-hydroxy-2-hydroxymethylethylamino, 2-hydroxyethylamino, 3-hydroxypropylamino, (RS), (R) or (5) 2,2-dimethyl-1,3-dioxolan-4-ylmethylamino, 2-hydroxy-1-hydroxymethylethylamino, 3-hydroxybutylamino, or tetrahydropyran-4-ylamino.

7. The compound of claim 1 wherein R$^1$ and R$^2$ are hydrogen; R$^4$ and R are at the 2 and the 6 positions of the phenyl ring and are independently of each other hydrogen or halogen; and R$^6$ is at the 3-position of the phenyl ring.

8. The compound of claim 7 wherein R$^3$ is alkyl or hydrogen,, R$^6$ is —OR$^8$ (wherein R$^8$ is heteroalkyl or heterocyclylalkyl), —NHR$^{10}$ (wherein R$^{10}$ is heteroalkyl, heterosubstituted cycloalkyl, heterocyclyl, or heterocyclylalkyl), or —X-(alkylene)-Y-heteroalkyl (wherein X is a covalent bond, —O— or —NH— and Y is —O— or —NH).

9. The compound of claim 8 wherein R$^3$ is methyl and R$^4$ and R$^5$ are independently of each other hydrogen, chloro, or fluoro.

10. The compound of claim 9 wherein R$^4$ and R$^5$ are hydrogen.

11. The compound of claim 10 wherein R$^1$ is (RS), (R) or (S) 2-hydroxy-2-hydroxymethyl-ethyloxy, 3-hydroxypropyloxy, 2-aminoethyloxy, 3-aminopropyloxy, 2-morpholin-4-ylethyloxy, or (RS), (R) or (S) 2,2-dimethyl-1,3-dioxolan-4-ylmethyloxy.

12. The compound of claim 10 wherein R$^6$ is (RS), (R) or (S) 2-hydroxy-2-hydroxymethylethylamino, 2-hydroxyethylamino, 3-hydroxypropylamino, (RS), (R) or (S) 2,2-dimethyl-1,3-dioxolan-4-ylmethylamino, 2-hydroxy-1-hydroxymethylethylamino, 3-hydroxybutylamino, or tetrahydropyran-4-ylamino.

13. The compound of claim 1 wherein R$^1$ is at the 5-position of the indole ring and is halo; R$^2$ is hydrogen; R$^4$ and R$^5$ are at the 2 and the 6 positions of the phenyl ring and are independently of each other hydrogen or halogen; and R$^6$ is at the 3-position of the phenyl ring.

14. The compound of claim 13 wherein R$^3$ is alkyl or hydrogen, , R$^6$ is —OR$^8$ (wherein R$^8$ is heteroalkyl or heterocyclylalkyl), —NHR$^{10}$ (wherein R$^{10}$ is heteroalkyl, heterocyclyl, or heterocyclylalkyl), or -X-(alkylene)-Y-heteroalkyl (wherein X is a covalent bond, —O— or —NH— and Y is —O— or —NH).

15. The compound of claim 14 wherein R$^1$ is chloro or fluoro; R$^3$ is methyl; and R$^4$ and R$^5$ are independently of each other hydrogen, chloro, or fluoro.

16. The compound of claim 15 wherein R$^6$ is (RS), (R) or (S) 2-hydroxy-2-hydroxymethyl-ethyloxy, 3-hydroxypropyloxy, 2-aminoethyloxy, 3-aminopropyloxy, 2-morpholin-4-ylethyloxy, or (RS), (R) or (S) 2,2-dimethyl-1,3-dioxolan-4-ylmethyloxy.

17. The compound of claim 14 wherein R$^6$ is (RS), (R) or (S) 2-hydroxy-2-hydroxymethylethylamino, 2-hydroxyethylamino, 3-hydroxypropylamnino, (RS), (R) or (S) 2,2-dimethyl-1,3-dioxolan-4-ylmethylamino, 2-hydroxy-1-hydroxymethylethylamino, 3-hydroxybutylamino, or tetrahydropyran-4-ylamino.

18. A pharmaceutical composition comprising a therapeutically effective amount of a compound of claim 1 and a pharmaceutically acceptable excipient.

19. A method of treating GSK-3β mediated diseases selected from Alzheimer's disease, obesity, diabetes, atherosclerotic cardiovascular disease, polycystic ovary syndrome, syndrome X, ischemia, traumatic brain injury, bipolar disorder, immunodeficiency, cancer, allergy, and asthma in a mammal which method comprises administration to the mammal a therapeutically effective amount of a compound of claim 1.

20. The method of claim 19 wherein the disease is asthma.

21. A method of treating a patient having a disease characterized by an excess of CD4+ Th2 cytokines, comprising administering to the patient a therapeutically effective amount of an inhibitor of GSK-3β.

22. The method of claim 21, wherein the GSK-3β inhibitor is a compound of claim 1.

23. The method of claim 21, wherein the disease is asthma, allergy or allergic rhinitis.

24. The method of claim 21, wherein the disease is asthma.

25. The method of claim 21, wherein the GSK-3β inhibitor is at least 10 fold more selective for GSK-3β relative to PKC.

26. A method of treating a patient having a disease characterized by an excess IgE production, comprising administering to the patient a therapeutically effective amount of an inhibitor of GSK-3β.

27. The method of claim 26, wherein the GSK-3β inhibitor is a compound of claim 1.

28. The method of claim 26, wherein the disease is asthma.

29. The method of claim 26, wherein the GSK-3β inhibitor is at least 10 fold more selective for GSK-3β relative to PKC.

30. A method for preparing a compound of Formula (I) which comprises: reacting a 3-indol-3-yl-4-phenylfuran-2,5-dione of formula:

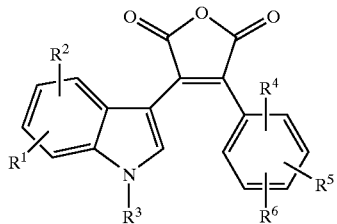

where $R^1-R^6$ are as defined in claim 1 with ammonia to provide a compound of Formula (I); or reacting a compound of the formula:

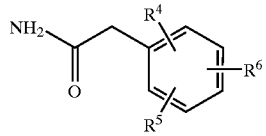

where $R^1-R^3$ are as defined in claim 1 and R is alkyl, with a compound of the formula:

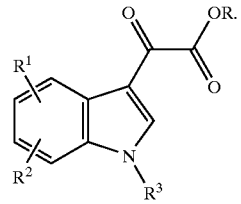

where $R^4-R^6$ are as defined in claim 1, in the presence of a base; and (iii) optionally converting a compound of Formula (I) to other compounds of Formula (I);

(iv) optionally converting the compound of Formula (I) prepared in Steps (i) or (ii) above, to the corresponding acid addition salt by treatment with an acid;

(v) optionally converting the compound of Formula (I) prepared in Steps (i) or (ii) above, to the corresponding free base by treatment with a base; and optionally separating a mixture of stereoisomers of a compound of Formula (I) prepared in Steps (i)–(v) above, to give a single stereoisomer.

* * * * *